US009926354B2

(12) United States Patent
Tan et al.

(10) Patent No.: US 9,926,354 B2
(45) Date of Patent: Mar. 27, 2018

(54) AMYLOID PRECURSOR PROTEIN (APP) BASED Ã#-SECRETASE INHIBITOR PEPTIDES, AND METHODS OF USE

(71) Applicant: UNIVERSITY OF SOUTH FLORIDA, Tampa, FL (US)

(72) Inventors: Jun Tan, Tampa, FL (US); Brian Nelson Giunta, Tampa, FL (US); Song Li, Tampa, FL (US); Huayan Hou, Tampa, FL (US); Paul R. Sanberg, Spring Hill, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 15/107,383

(22) PCT Filed: Jan. 9, 2015

(86) PCT No.: PCT/US2015/010813
§ 371 (c)(1),
(2) Date: Jun. 22, 2016

(87) PCT Pub. No.: WO2015/106098
PCT Pub. Date: Jul. 16, 2015

(65) Prior Publication Data
US 2017/0044225 A1 Feb. 16, 2017

Related U.S. Application Data

(60) Provisional application No. 61/925,492, filed on Jan. 9, 2014.

(51) Int. Cl.
*A61K 38/22* (2006.01)
*A61N 5/10* (2006.01)
*C12N 15/113* (2010.01)
*G01N 33/574* (2006.01)
*A61K 31/713* (2006.01)
*A61K 45/06* (2006.01)
*C07K 14/47* (2006.01)
*A61K 38/17* (2006.01)
*A61K 38/00* (2006.01)

(52) U.S. Cl.
CPC .......... *C07K 14/4711* (2013.01); *A61K 38/17* (2013.01); *A61K 38/00* (2013.01); *C07K 2319/10* (2013.01)

(58) Field of Classification Search
CPC .... A61K 38/00; A61K 38/17; C07K 2319/00; C07K 14/4711; C07K 2319/10
See application file for complete search history.

(56) References Cited

U.S. PATENT DOCUMENTS

2004/0018529 A1 1/2004 Li et al.
2006/0270841 A1* 11/2006 Espeseth ............... C07K 14/47
536/23.2
2009/0305968 A1 12/2009 Bonny
2013/0202680 A1 8/2013 Vigo et al.

FOREIGN PATENT DOCUMENTS

WO WO-2013/103964 A1 7/2013

OTHER PUBLICATIONS

Selkoe, "Translating cell biology into therapeutic advances in Alzheimer's disease", Nature, Jun. 24, 1999, pp. 23-31, vol. 399, 2000 Macmillan Magazines Ltd.
Sinha et al., "Cellular mechanisms of β-amyloid production and secretion", Proceedings of the National Academy of Sciences of the United States of America, Sep. 1999, pp. 11049-11053, vol. 96, Colloquium Paper, San Francisco, CA.
Games et al., "Alzheimer-type neuropathology in transgenic mice overexpressing V717F β-amyloid precursor protein," Nature, Feb. 9, 1995, pp. 523-527, vol. 373.
Higgins et al., "Transgenic mice and modeling Alzheimer's disease," Reviews in the Neurosciences, 1995, pp. 87-96, vol. 6, No. 3, Freund Publishing House Ltd., London.
Seiffert et al., "Presenilin-1 and -2 are molecular targets for γ-secretase inhibitors," The Journal of Biological Chemistry, Nov. 3, 2000, pp. 34066-34091, vol. 275, No. 44, JBC Papers in Press.
Wolfe et al., "Two transmembrane aspartates in presenilin-1 required for presenilin endoproteolysis and γ-secretase activity," Nature, Apr. 8, 1999, pp. 513-517, vol. 398, Macmillan Magazines Ltd.
Shen et al., "Skeletal and CNS defects in presenilin-1-deficient mice," Cell; May 16, 1997, pp. 629-639, vol. 89.
Wong et al., "Presenilin 1 is required for Notch1 and DII1 expression in the paraxial mesoderm," Nature, May 15, 1997, pp. 288-291, vol. 387.
Haass et al., "The presenilins in Alzheimer's disease—proteolysis holds the key," Science, Oct. 29, 1999, pp. 916-919, vol. 286.
Esler et al., "Transition-state analogue inhibitors of γ-secretase bind directly to presnilin-1," Nature Cell Biology; Jul. 2000, pp. 428-434, vol. 2, Macmillan Magazines Ltd.
Haass, "Take five—BACE and the γ-secretase quartet conduct Alzheimer's amyloid β-peptide generation," The EMBO Journal, Jan. 29, 2004, pp. 483-488, vol. 23, No. 3.
Coric et al., "Safety and tolerability of the γ-secretase inhibitor avagacestat in a phase 2 study of mild to moderate Alzheimer disease," Archives of Neurology, Nov. 2012, pp. 1430-1440, vol. 69.
Green et al., "Effect of tarenflurbil on cognitive decline and activities of daily living in patients with mild Alzheimer disease: a randomized controlled trial," JAMA: The Journal of the American Medical Association, Dec. 16, 2009, pp. 2557-2564, vol. 302, No. 23.
Doody et al., "A phase 3 trial of semagacestat for treatment of Alzheimer's disease," The New England Journal of Medicine, Jul. 15, 2013, pp. 341-350, vol. 369, No. 4.

(Continued)

Primary Examiner — Gregory S Emch
(74) Attorney, Agent, or Firm — Saliwanchik, Lloyd & Eisenschenk

(57) ABSTRACT

The present invention provides fusion peptides, compositions, methods and kits for treating, reducing the risk of, lessening the severity of, preventing, or delaying the onset of amyloid-related disorders, such as Alzheimer's disease and HIV associated neurocognitive impairment.

10 Claims, 15 Drawing Sheets

(56) References Cited

OTHER PUBLICATIONS

Schor, "What the halted phase III γ-secretase inhibitor trial may (or may not) be telling us," *Annals of Neurology*, Feb. 2011, pp. 237-239, vol. 69, No. 2.
Gupta et al., "Semagacestat for treatment of Alzheimer's disease," *The New England Journal of Medicine*, Oct. 24, 2013, pp. 1660-1661, vol. 369, No. 17.
Ohno et al., "BACE1 deficiency rescues memory deficits and cholinergic dysfunction in a mouse model of Alzheimer's disease," *Neuron*, Jan. 8, 2014, pp. 27-33, vol. 4.
Cai et al., "BACE1 is the major β-secretase for generation of Aβ peptides by neurons," *Nature Neuroscience*, Mar. 2001, pp. 233-234, vol. 4, No. 3, Nature Publishing Group.
Hong et al., "Structure of the protease domain of memapsin 2 (β-secretase) complexed with inhibitor," *Science*, Oct. 6, 2000, pp. 150-153, vol. 290, American Association for the Advancement of Science, Washington.
Zhu et al., "Discovery of cyclic acylguanidines as highly potent and selective β-site amyloid cleaving enzyme (BACE) inhibitors: part I—inhibitor design and validation," *Journal of Medical Chemistry*, Feb. 11, 2010, pp. 951-965, vol. 53, No. 3.
Wyss et al., "Combining NMR and x-ray crystallography in fragment-based drug discovery: discovery of high potent and selective BACE-1 inhibitors," *Top Curr. Chem*, 2012, pp. 83-114, vol. 317.
Ghosh et al., "BACE1 (β-secretase) inhibitors for the treatment of Alzheimer's disease," *Chemical Society Reviews*, Apr. 2, 2014, pp. 6765-6813, vol. 43.
Oehlrich et al., "The evolution of amidine-based brain penetrant BACE1 inhibitors," *Bioorganic & Medicinal Chemistry Letters*, May 1, 2014, pp. 2033-2045, vol. 24, Elsevier Ltd.
Evin et al., "BACE inhibitors as potential drugs for the treatment of Alzheimer's disease: focus on bioactivity," *Recent Patents on CNS Drug Discovery*, 2011, pp. 91-106, vol. 6, No. 2, Bentham Science Publishers.
Probst et al., "Small-molecule BACE1 inhibitors: a patent literature review (2006-2011)," *Expert Opinion on Therapeutic Patents*, May 2012, pp. 511-540, vol. 22, No. 5. Informa UK, Ltd.
Yan et al., "Targeting the β secretase BACE1 for Alzheimer's disease therapy," *Lancet Neurology*, Mar. 2014, pp. 319-329, vol. 13.
Luo et al., "Mice deficient in BACE1, the Alzheimer's β-secretase, have normal phenotype and abolished β-amyloid generation," *Nature Neuroscience*, Mar. 2001, pp. 231-232, vol. 4, No. 3, Nature Publishing Group.
Nishitomi et al., "BACE1 inhibition reduces endogenous Abeta and alters APP processing in wild-type mice," *Journal of Neurochemistry*, Dec. 2006, pp. 1555-1563, vol. 99.
Willem et al., "Control of peripheral nerve myelination by the β-secretase BACE1," *Science*, Oct. 27, 2006, pp. 664-666, vol. 314.
Giacobini et al., "Alzheimer disease therapy—moving from amyloid-β to tau," *Nature Reviews Neurology*, Dec. 2013, pp. 677-686, vol. 9, Macmillan Publishers Ltd.
Rezai-Zadeh et al., "Green tea epigallocatechin-3-gallate (EGCG) modulates amyloid precursor protein cleavage and reduces cerebral amyloidosis in Alzheimer transgenic mice," *The Journal of Neuroscience*, Sep. 21, 2005, pp. 8807-8814, vol. 25, No. 38.
Modi et al., "Relationship between helix stability and binding affinities: molecular dynamics simulations of Bfl-1/A1-binding pro-apoptotic BH3 peptide helices in explicit solvent," *Journal of Biomolecular Structure and Dynamics*. Jan. 1, 2013, pp. 65-77, vol. 31, No. 1, Taylor & Francis Group.
Schwarze et al., "In vivo protein transduction: delivery of a biologically active protein into the mouse," *Science*, Sep. 3, 1999, pp. 1569-1572, vol. 285, No. 5433.
Cao et al., "In vivo delivery of a Bcl-xL fusion protein containing the TAT protein transduction domain protects against ischemic brain injury and neuronal apoptosis, " *The Journal of Neuroscience*, Jul. 1, 2002, pp. 5423-5431, vol. 22, No. 13.
Zou et al., "Cell-penetrating peptide-mediated therapeutic molecule delivery into the central nervous system," *Current Neuropharmacology*, Mar. 2013, pp. 197-208, vol. 11, No. 2, Bentham Science Publishers.
Azzarito et al., "Inhibition of α-helix-mediated protein-protein interactions using designed molecules," *Nature Chemistry*, Mar. 2013, pp. 161-173, vol. 5, Macmillan Publishers Limited.
Rao et al., "Truncated and helix-constrained peptides with high affinity and specificity for the cFos coiled-coil of AP-1," *Plos One*, Mar. 27, 2013, pp. 1-12, vol. 8, No. 3.
Oakley et al., "Intraneuronal β-amyloid aggregates, neurodegeneration, and neuron loss in transgenic mice with five familial Alzheimer's disease mutations: potential factors in amyloid plaque formation," *The Journal of Neuroscience*, Oct. 4, 2006, pp. 10129-10140, vol. 26, No. 40.
Lin et al., "Human aspartic protease memapsin 2 cleaves the β-secretase site of β-amyloid precursor protein," *Proceedings of the National Academy of Sciences of the United States of America*, Feb. 15, 2000, pp. 1456-1460, vol. 97, No. 4.
Vassar et al., "β-secretase cleavage of Alzheimer's amyloid precursor protein by the transmembrane aspartic protease BACE," *Science*, Oct. 22, 1999, pp. 735-741, vol. 266, No. 5440.
Hussain et al., "Identification of a novel aspartic protease (Asp 2) as β-secretase," *Molecular and Cellular Neuroscience*, Dec. 1999, pp. 419-427, vol. 14.
Obregon et al., "Soluble amyloid precursor protein-α modulates β-secretase activity and amyloid-β generation," *Nature Communications*, Apr. 10, 2012. pp. 1-9, vol. 3, No. 777, Macmillan Publishers Limited.
Wong et al., "β subunits of voltage-gated sodium channels are novel substrates of β-site amyloid precursor protein-cleaving enzyme (BACE1) and γ-secretase," *The Journal of Biological Chemistry*, Jun. 17, 2005, pp. 23009-23017, vol. 280, No. 24.
Hu et al., "Bace1 modulates myeilnation in the central and peripheral nervous system," *Nature Neuroscience*, Dec. 2006, pp. 1520-1525, vol. 9, No. 12.
Tung et al., "Design of substrate-based inhibitors of human β-secretase," *Journal of Medicinal Chemistry*, Jan. 17, 2002, pp. 259-262, vol. 45, No. 2.
Cooper et al., "Peptide derived from HIV-1 TAT protein destabilizes a monolayer of endothelial cells in an in vitro model of the blood-brain barrier and allows permeation of high molecular weight proteins," *The Journal of Biological Chemistry*, Dec. 28, 2012, pp. 44676-44683, vol. 237, No. 53, USA.
Haass et al., "The Swedish mutation causes early-onset Alzheimer's disease by β-secretase cleavage within the secretory pathway," *Nature Medicine*, Dec. 1995, pp. 1291-1296, vol. 1, No. 12, Nature Publishing Group.
Thinakaran et al., "Metabolism of the "Swedish" amyloid precursor protein variant in neuro2a (N2a) cells. Evidence that cleavage at the "β-secretase" site occurs in the golgi apparatus," *The Journal of Biological Chemistry*, Apr. 19, 1996, pp. 9390-9397, vol. 271, No. 16.
International Search Report dated May 4, 2015 in International Application No. PCT/US2015/010813.

\* cited by examiner

SEQUENCE LISTING

```
<160> NUMBER OF SEQ ID NOS: 13

<210> SEQ ID NO 1
<211> LENGTH: 12
<212> TYPE: PRT
<213> ORGANISM: Homo sapiens

<400> SEQUENCE: 1

Glu Ile Ser Glu Val Asn Leu Asp Ala Glu Phe Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: viral

<400> SEQUENCE: 2

Tyr Gly Arg Lys Lys Arg Arg Gln Arg Arg Arg
1               5                   10

<210> SEQ ID NO 3
<211> LENGTH: 23
<212> TYPE: PRT
<213> ORGANISM: Artificial Sequence
<220> FEATURE:
<223> OTHER INFORMATION: human-virus fusion

<400> SEQUENCE: 3

Tyr Gly Arg Lys Lys Arg Arg Gln Arg Arg Arg Glu Ile Ser Glu Val
1               5                   10                  15

Asn Leu Asp Ala Glu Phe Arg
            20

<210> SEQ ID NO 4
<211> LENGTH: 12
<212> TYPE: PRT
<213> ORGANISM: Homo sapiens

<400> SEQUENCE: 4

Glu Ile Ser Glu Val Lys Met Asp Ala Glu Phe Arg
1               5                   10

<210> SEQ ID NO 5
<211> LENGTH: 16
<212> TYPE: PRT
<213> ORGANISM: Homo sapiens

<400> SEQUENCE: 5

Ile Lys Thr Glu Glu Ile Ser Glu Val Asn Leu Asp Ala Glu Phe Arg
1               5                   10                  15

<210> SEQ ID NO 6
<211> LENGTH: 27
<212> TYPE: PRT
<213> ORGANISM: Artificial Sequence
<220> FEATURE:
<223> OTHER INFORMATION: human-virus fusion

<400> SEQUENCE: 6

Tyr Gly Arg Lys Lys Arg Arg Gln Arg Arg Arg Ile Lys Thr Glu Glu
1               5                   10                  15

Ile Ser Glu Val Asn Leu Asp Ala Glu Phe Arg
            20                  25
```

```
<210> SEQ ID NO 7
<211> LENGTH: 16
<212> TYPE: PRT
<213> ORGANISM: Homo sapiens

<400> SEQUENCE: 7

Ile Lys Thr Glu Glu Ile Ser Glu Val Lys Met Asp Ala Glu Phe Arg
1               5                   10                  15

<210> SEQ ID NO 8
<211> LENGTH: 9
<212> TYPE: PRT
<213> ORGANISM: Homo sapiens

<400> SEQUENCE: 8

Glu Val Lys Met Asp Ala Glu Phe Arg
1               5

<210> SEQ ID NO 9
<211> LENGTH: 9
<212> TYPE: PRT
<213> ORGANISM: Homo sapiens

<400> SEQUENCE: 9

Glu Val Asn Leu Asp Ala Glu Phe Arg
1               5

<210> SEQ ID NO 10
<211> LENGTH: 27
<212> TYPE: PRT
<213> ORGANISM: Artificial Sequence
<220> FEATURE:
<223> OTHER INFORMATION: human-virus fusion

<400> SEQUENCE: 10

Tyr Gly Arg Lys Lys Arg Arg Gln Arg Arg Ile Lys Thr Glu Glu
1               5                   10                  15

Ile Ser Glu Val Lys Met Asp Ala Glu Phe Arg
            20                  25

<210> SEQ ID NO 11
<211> LENGTH: 23
<212> TYPE: PRT
<213> ORGANISM: Artificial Sequence
<220> FEATURE:
<223> OTHER INFORMATION: human-virus fusion

<400> SEQUENCE: 11

Tyr Gly Arg Lys Lys Arg Arg Gln Arg Arg Glu Ile Ser Glu Val
1               5                   10                  15

Lys Met Asp Ala Glu Phe Arg
            20

<210> SEQ ID NO 12
<211> LENGTH: 20
<212> TYPE: PRT
<213> ORGANISM: Artificial Sequence
<220> FEATURE:
<223> OTHER INFORMATION: human-virus fusion

<400> SEQUENCE: 12

Tyr Gly Arg Lys Lys Arg Arg Gln Arg Arg Glu Val Lys Met Asp
1               5                   10                  15
```

```
Ala Glu Phe Arg
        20

<210> SEQ ID NO 13
<211> LENGTH: 20
<212> TYPE: PRT
<213> ORGANISM: Artificial Sequence
<220> FEATURE:
<223> OTHER INFORMATION: human-virus fusion

<400> SEQUENCE: 13

Tyr Gly Arg Lys Lys Arg Arg Gln Arg Arg Arg Glu Val Asn Leu Asp
1               5                   10                  15

Ala Glu Phe Arg
        20
```

AMYLOID PRECURSOR PROTEIN (APP) BASED Ã#-SECRETASE INHIBITOR PEPTIDES, AND METHODS OF USE

CROSS-REFERENCE TO RELATED APPLICATION

This application is the U.S. national stage application International Patent Application No. PCT/US2015/010813, filed Jan. 9, 2015, which claims priority to U.S. application No. 61/925,492, filed Jan. 9, 2014, the disclosure of each of which are incorporated herein by reference in their entirety.

GOVERNMENT SUPPORT

This invention was made with government support under Grant Numbers R01AG032432 and R01AT007411 awarded by National Institutes of Health. The government has certain rights in the invention.

BACKGROUND OF INVENTION

The proteolysis of the type 1 membrane-anchored amyloid precursor protein (APP) by the sequential actions of β- and γ-secretases results in amyloid-β (Aβ) peptide production that is thought to be causal for Alzheimer's disease (AD), cerebral amyloid angiopathy (CAA), certain forms of HIV associated neurocognitive impairment (HAND), certain forms of Lewy body dementia, inclusion body myositis, and certain forms of mild cognitive impairment (MCI) (Selkoe, 1999; Sinha et al., 1999; Games et al., 1995; Higgins et al., 1995). Inhibition or modulation of β- and/or γ-secretases constitutes important therapeutic strategies for AD and has become the centerpiece of therapeutically oriented research on this disease.

Presenilin 1 and 2 (PS1 and PS2), two integral membrane proteins found in the endoplasmic reticulum and Golgi apparatus, are the major enzymatic targets for γ-secretase inhibition for the treatment of AD (Seiffert et al., 2000). However, apart from their roles in AD, PS1 and PS2 also control the Notch signaling pathway responsible for cell proliferation and differentiation during embryonic development (Wolfe et al., 1999). PS1/2 knockout mice have massive neuronal loss, skeletal defects, underdeveloped subventricular areas and severe hemorrhages, and only a few types of PS1/2 knockout mouse models could survive after birth (Shen et al., 1997; Wong et al., 1997; Haass et al., 1999; Ester et al., 2000). Other substrates of PS1/2 have also been identified, suggesting pleotropic function of the PSs (Haass, 2004). Most importantly, recent clinical trials have indicated that the inhibition of γ-secretase is likely to cause undesirable side effects (Coric et al., 2012). Indeed, several such inhibitors, including avagacestat (Bristol-Myers Squibb), tarenflurbil (Flurizan, Myriad Genetics), and semagacestat (Eli Lilly and Co.), have failed to complete Phase 3 clinical trials (Cork et al., 2012; Green et al., 2009; Doody et al., 2013; Schor, 2011; Gupta, 2013). In the case of semagacestat, activities of daily living and cognition even worsened in treated patients (Doody et al., 2013; Schor, 2011; Gupta, 2013).

Like γ-secretase, β-secretase, widely known as β-site amyloid precursor protein cleaving enzyme 1 (BACE1), has also been identified as a prime therapeutic target for AD intervention. Its inhibition would halt the formation of Aβ at the first step of APP amyloidogenic processing. The therapeutic potential of BACE1 has been confirmed, e.g. genetic inhibition of the enzyme rescues memory deficits in AD model animals, (Ohno et al., 2004) and BACE1-deficient neurons fail to secrete Aβ peptides or generate β-C terminal fragment (β-CTF) (Cai et al., 2001). In view of these strong in vivo and in vitro validations of critical roles of BACE1 in Aβ generation and AD pathology, intense efforts are underway in both academia and industry to develop potent inhibitors of BACE1. Most of the early BACE1 inhibitors were non-cleavable peptide-based transition state analogues modeled after the β-secretase cleavage site of APP (Hong et al., 2000).

Unfortunately, while these peptidomimetic BACE1 inhibitors show dramatic impacts on Aβ generation in vitro, the majority of these inhibitors tend to possess poor drug-like properties in vivo, due to poor oral bioavailability, short serum half-life, or low blood-brain barrier (BBB) penetration. More recently, a number of non-peptidomimetic candidates for BACE1 inhibitors have been developed, including carbinamincs, acylguanidines, aminoquinazolines, and aminothiazines (Zhu et al., 2010; Wyss et al., 2012; Ghosh et al., 2014; Oehlrich et al., 2014). The less BBB penetration has also been solved with the development of potent third-generation small-molecule BACE1 inhibitors that exhibit satisfactory pharmacokinctics profiles and robust cerebral Aβ reduction in preclinical tests (Evin et al., 2011; Probst et al., 2012). As a result, several BACE1 inhibitors have entered clinical trials, including MK8931 (Merck), LY2886721 (Eli Lilly and Co.) and E2609 (Eisai) (Yan et al., 2014).

BRIEF SUMMARY

The present invention addresses the need for attenuation of Aβ production in individuals with a mutant "Swedish" form of APP or the wild type form of APP to prevent or treat onset/progression of amyloid-related disorders, such as but not limited to Alzheimer's disease (AD) and HIV associated neurocognitive impairment (HAND).

In one aspect, APP-Tat fusion peptides comprising the amino acid sequence of SEQ ID NO: 3 are provided. Furthermore, in some aspects, a therapeutically effective amount of the peptides comprising the amino acid sequence of SEQ ID NO: 3 are included in pharmaceutical compositions comprising one or more pharmaceutically acceptable carriers.

In another aspect, methods of treating, reducing the risk of, lessening the severity of, preventing or delaying the onset of an amyloid-related disorder are provided. The methods comprise administering a therapeutically effective amount of one or more APP-Tat fusion peptides to a subject having the disorder, or who is at risk of developing the disorder. In some embodiments, the APP-Tat fusion peptides comprise a fragment of APPswe linked to a fragment of the HIV Tat protein transduction domain. In some embodiments, the subject is a human. Furthermore, in some embodiments, the APPswe-Tat fusion peptides are combined with one or more pharmaceutically acceptable carriers.

In some embodiments, the fragment of the APPswe comprises the amino acid sequence of SEQ ID NO: 1. In some embodiments, the fragment of the HIV Tat protein transduction domain comprises the amino acid sequence of SEQ ID NO: 2. In other embodiments, the APP-Tat fusion peptide comprises the amino acid sequence of SEQ ID NO: 3, or a fragment thereof.

In some embodiments, the amyloid-related disorder is a neurological disease such as, but not limited to, AD, HAND, Lewy body dementia, CAA, inclusion body myositis, and MCI.

In another aspect, peptides comprising the amino acid sequence of SEQ ID NO: 3, or a fragment thereof, are provided in one or more cultured cells.

In another aspect, kits are provided that comprise APP-Tat fusion peptides (or pharmaceutical compositions containing one or more of the fusion peptides of the present invention), one or more reagents, and instructions for use thereof. In some embodiments, the APP-Tat fusion peptides utilized in kits comprise the amino acid sequence of SEQ ID NO: 3, or fragments thereof.

The methods, compositions and kits herein described can be used in connection with pharmaceutical, medical, and veterinary applications, as well as fundamental scientific research and methodologies, as would be apparent to a skilled person upon reading of the present disclosure. These and other objects, features and advantages of the present invention will become clearer when the drawings as well as the detailed description are taken into consideration.

BRIEF DESCRIPTION OF DRAWINGS

For a fuller understanding of the nature of the present invention, reference should be had to the following detailed description taken in connection with the accompanying drawings.

BRIEF DESCRIPTION OF THE SEQUENCES

Figure 1:
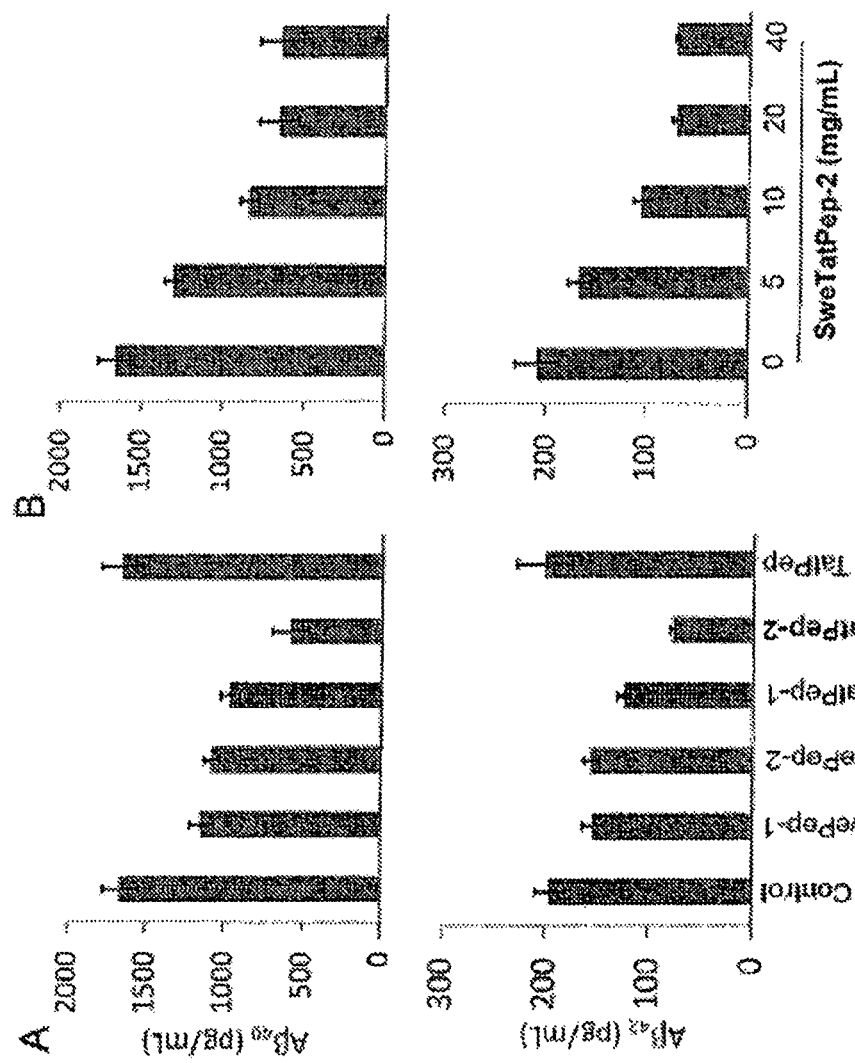
FIG. 1 shows ELISA results for (A) Aβ production in cultured media of CHO/APPwt cells treated with control, Swedish peptide-1 (SwePep-1), Swedish peptide-2 (SwePep-2), Swedish Tat fusion peptide-2 (SweTatPep-1, or Swedish Tat fusion peptide-2 (SweTatPep-2) at 20 μg/mL for 4 hours and (B) Aβ production in cultured media of CHO/APPwt cells treated with SweTatPep-2 at a range of doses for 4 hours.

SEQ ID NO: 1 is an amino acid sequence of an amyloid precursor protein fragment useful according to the present invention.

SEQ ID NO: 2 is an amino acid sequence of an HIV Tat protein transduction domain fragment useful according to the present invention.

SEQ ID NO: 3 is an amino acid sequence of a fusion peptide useful according to the present invention, the peptide comprising an amyloid precursor protein fragment and an HIV Tat protein transduction domain fragment.

SEQ ID NO: 4 is an amino acid sequence of an amyloid precursor protein fragment useful according to the present invention.

SEQ ID NO: 5 is an amino acid sequence of an amyloid precursor protein fragment useful according to the present invention.

SEQ ID NO: 6 is an amino acid sequence of a fusion peptide useful according to the present invention, the peptide comprising an amyloid precursor protein fragment and an HIV Tat protein transduction domain fragment.

SEQ ID NO: 7 is an amino acid sequence of an amyloid precursor protein fragment useful according to the present invention.

SEQ ID NO: 8 is an amino acid sequence of an amyloid precursor protein fragment useful according to the present invention.

SEQ ID NO: 9 is an amino acid sequence of an amyloid precursor protein fragment useful according to the present invention.

SEQ ID NO: 10 is an amino acid sequence of a fusion peptide useful according to the present invention, the peptide comprising an amyloid precursor protein fragment and an HIV Tat protein transduction domain fragment.

SEQ ID NO: 11 is an amino acid sequence of a fusion peptide useful according to the present invention, the peptide comprising an amyloid precursor protein fragment and an HIV Tat protein transduction domain fragment.

SEQ ID NO: 12 is an amino acid sequence of a fusion peptide useful according to the present invention, the peptide comprising an amyloid precursor protein fragment and an HIV Tat protein transduction domain fragment.

SEQ ID NO: 13 is an amino acid sequence of a fusion peptide useful according to the present invention, the peptide comprising an amyloid precursor protein fragment and an HIV Tat protein transduction domain fragment.

DETAILED DISCLOSURE

The present invention is directed to fusion peptides, compositions, methods, and kits for treating, reducing the risk of, lessening the severity of, preventing, or delaying the onset of an amyloid-related disorder, such as Alzheimer's disease (AD).

As β-secretase 1 (BACE1) is one of two enzymes responsible for Aβ generation (a pathology of Alzheimer's disease (AD); cerebral amyloid angiopathy (CAA), certain forms of HIV associated neurocognitive impairment (HAND); certain forms of Lewy body dementia; inclusion body myositis; and certain forms of mild cognitive impairment (MCI)), there is a need to modulate this enzyme without adverse side-effects (Lin et al., 2000; Sinha et al. 1999; Vassar et al. 1999; Yan et al. 1999; Selkoe 1999) as seen with clinical trials of previous BACE inhibitors. Aβ is formed from the progressive cleavage of type 1 membrane-anchored amyloid precursor protein (APP) by β- and γ-secretases. Many Aβ peptides are formed from APP proteolysis, among the most neurotoxic being $A\beta_{40}$ and $A\beta_{42}$. Effective modulation of BACE1 has been difficult because it cleaves multiple substrates (Hemming et al., 2009). Familial AD is caused by mutations at codons 670 and 671 of APP. The mutant "Swedish" form of the APP (APPswe) β-site is of higher affinity to BACE1 compared to wild type APP (APPwt) and thus a higher proportion of APP molecules are processed during maturation (Haass et al., 1995; Thinakaran et al., 1996) into Aβ promoting subsequent amyloid-related disorders.

Compared to γ-secretase, initial reports have indicated that BACE1-null mice were viable, fertile, and devoid of abnormalities, suggesting that inhibition of this enzyme could be clinically feasible with few mechanistic side effects (Luo et al., 2001; Nishitomi et al., 2006). However, subsequent investigations found that BACE1 is also a multi-substrate enzyme and identified more than several abnormalities in BACE1-null mice (Yan et al., 2014; Willem et al., 2006). Although these BACE1-null abnormalities are relatively mild, they are complex neurological phenotypes that raise a concern that complete inhibition or entire absence of BACE1 function may not be free of mechanism-based side effects.

In fact, a phase II clinical trial of the promising LY2886721 inhibitor of BACE1 was suspended in June 2013 by Eli Lilly and Co. due to possible liver toxicity (Yan et al., 2014; Giacobini et al., 2013). Thus, while these classes of non-peptide type BACE1 inhibitors utilize novel interactions with both the catalytic machinery and the specificity pockets of BACE1, combining potency, selectivity and the desired safety profiles remains to be a continued challenge. Hence, there is still a clear need for novel biochemical research for development of potent, selective BACE1 inhibitors with properties optimal for central nervous system therapeutics.

To address this need, one aspect of the present invention provides a novel substrate-based peptidomimetic BACE1 inhibitor termed "APPswe BACE1 binding site peptide (APPsweBBP)." This peptide is a 12-AA-residue fragment derived from human Swedish mutant APP (APPswe), containing APPsweβ-cleavage sites (Glu665-Arg676 of APPswe770 iso form). Since APPswe has higher affinity for BACE1 compared to human wild-type APP (APPwt), it was hypothesized that BACE1 would preferentially proteolyze APPswe, as opposed to APPwt. To exclude the epitope of Aβ being produced, APPsweBBP was constructed to lack the intact Aβ domain. In order to develop this specific modulator against BACE1-mediated APP cleavage, peptides derived from the APPswe or APPwt genes were screened and APPsweBBP was found to be the most effective BACE1 inhibitor using a cell-free assay. In order to improve BBB permeability of APPsweBBP, the peptide was further conjugated with the membrane fusion fragment of HIV-1 Tat protein (Rezai-Zadch et al., 2005; Modi et al., 2013), which has been demonstrated to promote delivery through the cell membrane as well as the BBB (Schwarze et al., 1999; Cao et al., 2002; Zou et al., 2013). The BACE1 inhibitory and anti-amyloidogenic activities of the fusion protein (TAT-APPsweBBP) were further evaluated both in vitro and in vivo. As such, aspects of the present invention provide a competitive and selective modulator, and related methods and kits, for BACE1-mediated APP-cleavage that significantly decreases APP-specific BACE1 proteolytic function.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

The terminology used herein is for the purpose of describing particular embodiments only and is not intended to be limiting of the invention. As used herein, the indefinite articles "a", "an" and "the" should be understood to include plural reference unless the context clearly indicates otherwise.

The phrase "and/or," as used herein, should be understood to mean "either or both" of the elements so conjoined, i.e., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, i.e., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "subject" refers to any animal (e.g., mammals, birds, reptiles, amphibians, fish), including, but not limited to, humans, non-human primates, rodents, and the like, which is to be the recipient of a particular treatment. Preferably, a subject refers to a human. Typically, the terms "subject" and "patient" may be used interchangeably herein in reference to a subject. Furthermore, transgenic animals (e.g., transgenic rats and mice) are useful in the methods and kits of the present invention.

As used herein, the term "fragment" refers to a portion of a polypeptide or composition. For example, when referring to a protein, a fragment is a plurality of consecutive amino acids comprising less than the entire length of the polypeptide. For instance, a fragment of a compound can share up to 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% of its sequence with the parent compound.

As used herein, "disorder" refers to a disease, disorder or condition, or other departure from healthy or normal biological activity, and the terms can be used interchangeably. The terms would refer to any condition that impairs normal function. The condition may be caused by sporadic or heritable genetic abnormalities. The disease may be present in a subject with clinical or sub-clinical symptoms; however, the subject may also be asymptomatic at the time of diagnosis. In at least one embodiment, the disorders applicable to the fusion peptides and compositions of the present invention include amyloid-related disorders characterized by high levels of Aβ generation and accumulation. In preferred embodiments, the disorders being treated by peptides and compositions of the present invention include, but are not limited to, AD, HAND, CAA, Lewy body dementia, inclusion body myositis, and MCI.

As used herein, "treatment" or "treating" or "treat" refers to arresting or inhibiting, or attempting to arrest or inhibit, the development or progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disease, and similarly, various clinical and scientific methodologies and assays may be used to assess the reduction, regression, or remission of a disease or its symptoms. "Treatment" may refer to both therapeutic treatment and prophylactic or preventative measures. Those in need of treatment can include those already with the disease as well as those prone to have the disease or those in whom the disease is to be prevented. In at least one embodiment, the disease being treated is an amyloid-related disorder.

The terms "effective amount" and "therapeutically effective amount," used interchangeably, as applied to the fusion peptides and pharmaceutical compositions described herein, mean the quantity necessary to render the desired therapeutic result. For example, an effective amount is a level effective to treat, cure, or alleviate the symptoms of a disorder for which the fusion peptide, or composition thereof, is being administered. Amounts effective for the particular therapeutic goal sought will depend upon a variety of factors including the disorder being treated and its severity and/or stage of development/progression; the bioavailability and activity of the specific fusion peptide or pharmaceutical composition used; the route or method of administration and introduction site on the subject; the rate of clearance of the specific peptide or composition and other pharmacokinetic properties; the duration of treatment; inoculation regimen; drugs used in combination or coincident with the specific peptide or composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for an individual patient.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

The HIV-Tat (Trans-Activator of Transcription) contains a protein transduction domain, and is well known to penetrate cells with high efficiency (Schwarze et al., 2000). The amino acid sequence of the protein transduction domain is YGRKKRRQRRR (SEQ ID NO: 2) (Schwarze et al., 2000). The nuclear localization signal found within the domain, GRKKR, further enhances translocation of Tat into the cell nucleus (Ruben et al., 1989, Hauber et al., 1989). HIV Tat consists of between 86 and 101 amino acids depending on the subtype.

The present invention utilizes the BACE1 affinity of the APPswe substrate and the nuclear translocation abilities of Tat to draw the BACE1 enzyme away from the endogenous APPwt substrate and toward the novel APPswe protein which lacks the Aβ domain. Thus, Swedish APP-Tat fusion peptides have the potential to attract APPswe to BACE1, resulting in attenuation of Aβ production from endogenous APP, while leaving the Swedish mutation sites of APPswe free to bind the BACE1 β-cut site specifically with high affinity. With this specificity, there are few to no adverse effects since only the APPswe β-cut site is affected; leaving the endogenous APP protein free for normal α-secretase processing.

APP-Tat Fusion Peptides

The APP-Tat fusion peptides of the present invention comprise a fragment of a mutant amyloid precursor protein (APP) and a fragment of an HIV Tat protein transduction domain. Mutant APP utilized in the present invention may include amyloid like protein (APLP) mutants or other mutants from the APP gene family including, but not limited to, the "Swedish" mutation (APP with the double mutation Lys67β->Asn and Met671->Leu) and presenilin 1 mutations. In some embodiments, the mutant APP fragment utilized in APP-Tat fusion peptides of the present invention includes the amino acid sequence of SEQ ID NO:1 (EISEVNLDAEFR), or fragment thereof; and the HIV Tat protein transduction domain fragment includes the amino acid sequence of SEQ ID NO:2 (YGRKKRRQRRR), or fragment thereof. In further embodiments, the APP-Tat fusion peptide sequence comprises the amino acid sequence of SEQ ID NO:3 (YGRKKRRQRRREISEVNLDAEFR), or a fragment thereof. In additional embodiments, several APP wild type (APPwt) and APP mutant (APPswe) peptides, either alone or as fusions with a Tat peptide (as shown in Tables 1 and 2), are useful in the present invention for either controls in experimentation or as functional peptides according to the methods described herein. The highlighted residues in each of SEQ ID NOS: 1 and 3 represent the "Swedish" double mutation Lys67β->Asn and Met671->Leu (the Swedish mutation is also in SEQ ID NOS: 5 and 6).

The present invention also provides pharmaceutical compositions comprising APP-Tat fusion peptides in combination with one or more pharmaceutically acceptable carriers described herein.

The term "carrier" refers to a diluent, adjuvant, excipient, and/or vehicle with which the fusion peptide is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition may also contain wetting or emulsifying agents or suspending/diluting agents, or pH buffering agents, or agents for modifying or maintaining the rate of release of the fusion peptide. These compositions can take the form of solutions, suspensions, emulsion, tablets, pills, capsules, powders, sustained-release formulations and the like. Formulations can include standard carriers such as pharmaceutical grades of mannitol, lactose, sodium saccharine, starch, magnesium stearate, cellulose, magnesium carbonate, etc. Such compositions will contain a therapeutically effective amount of the fusion peptide together with a suitable amount of carrier so as to provide the proper form to the subject based on the mode of administration to be used.

Additionally, the fusion peptides and/or pharmaceutical compositions may be packaged with additional agents, such as therapeutic agents. The additional agents may be conjugated to the fusion peptides or packaged within a pharmaceutical composition comprising the fusion peptide.

The present invention also provides kits comprising an APP-Tat fusion peptide as described herein. The kits may be used in the methods described herein. The kits may also include at least one reagent and/or instructions for their use. Also, kits may include one or more containers filled with reagent(s) and/or one or more components of the pharmaceutical compositions of the invention. One or more container of the kits provided may also comprise a fusion peptide of the invention, preferably in a purified form. The kits may also comprise a control composition, such as positive and/or negative control peptides and/or antibodies.

In certain embodiments, the kits may additionally include reagents and means for detecting the binding of the fusion peptides to β-secretase and/or other receptor proteins of interest. The means of allowing detection may be by conjugation of detectable labels or substrates, such as fluorescent compounds, enzymes, radioisotopes, heavy atoms, reporter genes, luminescent compounds, or antibodies against the individual peptide components of the APP-Tat fusion peptide. As it would be understood by those skilled in the art, additional detection or labeling methodologies may be utilized in the kits provided.

Treatment Methods Utilizing APP-Tat Fusion Peptides

Aspects of the present invention are further directed to methods of treating, reducing the risk of, lessening the severity of, preventing, or delaying the onset of an amyloid-related disorder. The methods include administering to a subject, such as a mammal (e.g., a human), having an amyloid-related disorder, or at risk of such a disorder, a therapeutically effective amount of an APP-Tat fusion peptide, i.e. the APP-Tat fusion peptide including a fragment of a mutant amyloid precursor protein (APP) and a fragment of an HIV Tat protein transduction domain.

In some embodiments of methods provided herein, the APP-Tat fusion peptides include a mutant APP fragment with the amino acid sequence of SEQ ID NO: 1, or fragment thereof, and an HIV Tat protein transduction domain fragment with the amino acid sequence of SEQ ID NO: 2, or fragment thereof. In further embodiments, the APP-Tat fusion peptide sequence comprises the amino acid sequence of SEQ ID NO: 3, or fragment thereof.

Administration may be locally (confined to a single cell or tissue) and/or systemically in the subject. When administering a peptide, particularly a fusion peptide of the invention, care must be taken to use materials which do not absorb the peptide, thus allowing for effective release, or delayed release if so desired by the materials used. In some embodiments, the fusion peptide or pharmaceutical composition can be delivered in a controlled release system. Such methods may include the use of a pump for administration (e.g., use of an intravenous drip).

The fusion peptides and compositions of the invention can be used to treat, alleviate, inhibit, delay or prevent amyloid-related disorders characterized by high levels of Aβ generation and accumulation. In some embodiments, the disorder being treated includes, but is not limited to, AD, HAND, Lewy body dementia, CAA, inclusion body myositis, and mild cognitive impairment The fusion peptides of the invention can also be utilized in pharmaceutically acceptable compositions in the methods provided herein.

As would be understood by those skilled in the art, the amyloid-related disorders being treated would not necessarily need to have aberrant accumulation of Aβ; the Aβ levels may be within a normal range, yet the APP-Tat peptides of the invention may provide a means for modulation of the desired therapeutic or preventative response in the cell, surrounding cells and/or body of the subject being treated.

Furthermore, it would be understood by those skilled in the art that the therapeutic methods described would not only apply to treatment in a subject, but could be applied to cell cultures, organs, tissues, or individual cells in vivo, ex vivo or in vitro.

It would also be understood by a skilled artisan how to use the fusion peptides of the present invention for diagnostic or therapeutic purposes without undue experimentation based on the teachings provided throughout the specification.

A fusion peptide of the invention can also be utilized in combination with other fusion peptides of the invention (e.g., other APP-Tat fusions), antibodies, cholinesterase inhibitors, glutamate regulators, vaccines, gene therapies, neurotransmitter regulators, etc. during treatment. Such combination treatments may further enhance the therapeutic effects of treatment with the fusion peptides of the invention. The other treatments may also be carried out by linking the treatment modality (e.g., gene therapy vector or chemical compound) to the fusion peptide (i.e., fusion of the components), when applicable.

The amount of the fusion peptide or pharmaceutical compound of the invention which will be effective in the treatment, inhibition and/or prevention of an amyloid-related disorder can be determined by standard clinical techniques. Additionally, in vitro assays may be employed to help identify optimal dosage ranges. The precise dose to be utilized will also depend on the route of administration, and the seriousness of the disorder, and should also be decided according to the sound medical judgment of the clinician and each patient's individual circumstances. The specific therapeutically effective dose level for any particular patient will depend upon a variety of factors including: the type and degree of the response to be achieved; the specific composition and other agent(s), if any, employed; the age, weight, general health, sex, and diet of the patient; the time of administration, route of administration, and rate of excretion of the composition; the duration of the treatment; other drugs used in combination or coincidental with the fusion peptide/composition; and any other factors well known in the medical arts. Effective dosages may also be extrapolated from dose-response curves derived from in vitro or animal model testing systems.

Thus, the following non-limiting embodiments are provided:

1. A method of treating, reducing the risk of, lessening the severity of, preventing, or delaying the onset of an amyloid-related disorder, the method comprising administering to a subject having the disorder, or who is at risk of the disorder, a therapeutically effective amount of an APP-Tat fusion peptide, the APP-Tat fusion peptide comprising a fragment of a mutant amyloid precursor protein (APP) and a fragment of an HIV Tat protein transduction domain.

2. The method according to embodiment 1, wherein the fragment of the mutant amyloid precursor protein comprises the amino acid sequence of SEQ ID NO: 1.

3. The method according to embodiments 1-2, wherein the fragment of an HIV Tat protein transduction domain comprises the amino acid sequence of SEQ ID NO: 2.

4. The method according to embodiments 1-3, wherein the APP-Tat fusion peptide comprises the amino acid sequence of SEQ ID NO: 3, or a fragment thereof.

5. The method according to embodiments 1-4, wherein the subject is human.

6. The method according to embodiments 1-5, wherein the amyloid-related disorder is a neurological disease.

7. The method according to embodiments 1-6, wherein the amyloid-related disorder is selected from the group consisting of Alzheimer's disease, HIV associated neurocognitive impairment, Lewy body dementia, cerebral amyloid angiopathy, inclusion body myositis, and mild cognitive impairment.

8. The method according to embodiments 1-7, wherein the subject is at risk of developing an amyloid-related disorder.

9. The method according to embodiments 1-8, wherein the APP-Tat fusion peptide is in a pharmaceutically acceptable carrier.

10. A peptide comprising the amino acid sequence of SEQ ID NO: 3, or a fragment thereof.

11. A cultured cell comprising the peptide of embodiment 10.

12. A pharmaceutical composition comprising a therapeutically effective amount of an APP-Tat fusion peptide and a pharmaceutically acceptable carrier, the APP-Tat fusion peptide comprising a fragment of a mutant amyloid precursor protein (APP) and a fragment of an HIV Tat protein transduction domain.

13. The composition according to embodiment 12, wherein the fragment of the mutant amyloid precursor protein comprises the amino acid sequence of SEQ ID NO: 1.

14. The composition according to embodiments 12-13, wherein the fragment of an HIV Tat protein transduction domain comprises the amino acid sequence of SEQ ID NO: 2.

15. The composition according to embodiments 12-14, wherein the APP-Tat fusion peptide comprises the amino acid sequence of SEQ ID NO: 3, or a fragment thereof.

16. A kit comprising an APP-Tat fusion peptide and one or more reagents.

17. The kit according to embodiment 16, wherein the APP-Tat fusion peptide comprises the amino acid sequence of SEQ ID NO: 3, or a fragment thereof.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

EXAMPLES

The methods, peptides and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented.

In order to facilitate understanding of the following examples, certain frequently occurring materials and methods are described below.

Peptide Synthesis and Antibodies—All peptide sequences were commercially synthesized by GenScript Corporation (Piscataway, N.J., USA). Antibodies used included mouse anti-BACE1 (Merck Millipore, Darmstadt, Germany), rabbit anti-biotin (Cell Signaling, Beverly, Mass., USA), anti-N-terminal Aβ antibody (6E10, Covance, Emeryville, Calif.), anti-Aβ$_{16\text{-}26}$ antibody (4G8, Covance), anti-APP C-terminal antibody (pAb751/770, EMD Biosciences, La Jolla, Calif., USA), polyclonal anti-ADAM10 antibody (Merck Millipore), anti-ADAM17 antibody (TACE; Sigma-Aldrich, St Louis, Mo., USA), anti-Akt and phospho-Akt$^{Ser473}$ antibodies (Cell Signaling), rabbit anti-myelin basic protein (MBP) antibody (Sigma-Aldrich), and anti-β-actin antibody (Sigma-Aldrich).

BACE1 Activity Assay—The BACE1 inhibiting activity of APP-based BACE1 site binding peptides were determined using a fluorescence resonance energy transfer (FRET) assay (Pan Vera Co., Madison, Wis., USA), which employs a recombinant baculovirus-expressed BACE1 and a specific substrate (Rh-EVNLDAEFK-quencher) that is based on the APPswe mutation. This specific peptide substrate becomes highly fluorescent upon enzymatic cleavage. A mixture of 10 μL of BACE1 (1.0 U/mL in 50 mM Tris, pH7.5, 10% glycerol), 10 μL of FRET-substrate, and 10 μL of the various APP-based BACE1 site binding peptides (final concentration 20 μM) were incubated for 90 minutes in the dark at room temperature. Then, 10 μL of BACE1 stop buffer (2.5 M sodium acetate) was added to the mixture. Fluorescence was read using a fluorometer, with excitation at 545 nm and emission at 585 nm.

In order to confirm that APPsweBBP containing the β-cleavage site could bind to and be consequently proteolyzed by BACE1, 10 μg of biotin-labeled TAT-APPsweBBP was incubated with or without 10 μL of recombinant BACE1 protein (1.0 U/mL) in BACE1 reaction buffer for 4 hours at 37° C. and then subjected to Western blot (WB) analysis as described previously (Rezai-Zadeh et al., 2005; Obregon et al., 2012). In addition, immunoprecipitation (IP) and WB analyses of this mixture was performed with anti-BACE1 and anti-biotin antibodies to confirm that TAT-APPsweBBP, but not TAT, specifically binds to BACE1.

Cell Culture—Chinese hamster ovary (CHO) cells engineered to express wild-type human APP (CHO/APPwt cells) or Swedish mutant human APP (CHO/APPswe cells) were kindly provided by Dr. Stefanie Hahn and Dr. Sascha Weggen (University of Heinrich Heine, Dusseldorf, Germany). As described previously (Obregon et al., 2012), these cells were cultured in Dulbecco's modified Eagle's medium (DMEM) with 10% fetal bovine serum (FBS), 1 mM sodium pyruvate, and 100 units/mL of penicillin and streptomycin.

To confirm the binding of APPsweBBP with BACE1, CHO/APPwt cells were plated in 8-well chambers ($5\times10^5$/well), incubated with TAT-APPsweBBP-biotin or APPsweBBP-biotin at 20 μM for 30 minutes, fixed with 4% paraformaldehyde for 20 minutes, washed and permeabilized with 0.5% Triton X-100. Following application of blocking buffer, these cells were stained with mouse anti-BACE1 and rabbit anti-biotin antibodies overnight at 4° C. for immunocytochemistry analysis. In order to determine the inhibitory effects of TAT-APPsweBBP on BACE1-mediated APP β-cleavage and subsequent Aβ production, both CHO/APPwt and CHO/APPswe cells were plated in 24 well-plates ($3\times10^5$/well) and treated with TAT-APPsweBBP at 0-20 μM for 24 hours. The cultured media were collected for Aβ analysis by enzyme-linked immunosorbent assay (ELISA) and sAPPα analysis by ELISA and Western blot (WB). Cell lysates were also prepared for analysis of APP amyloidogenic processing by WB.

5XFAD Mice—Transgenic AD mice [5XFAD; B6SJL-Tg (APPSwFlLon,PSEN1*M146L*L286V) 6799Vas/Mmjax] at 2.5 months of age were obtained from the Jackson Laboratory (Bar Harbor, Me., USA) and housed and maintained in the Animal Facility of College of Medicine at University of South Florida. The mice at 3.5 months of age were treated with TAT-APPsweBBP, TAT peptide (100 nM/kg in 100 μl PBS) or PBS (100 μl) intraperitoneally (i.p.) daily for eight consecutive weeks. The mice were subjected to behavioral testing after 8 week-treatment and euthanized for immunohistochemical, ELISA and WB analysis after completing behavioral tests. All experiments involving mice were in compliance with the U.S. Department of Health and Human Services Guide for the Care and Use of Laboratory Animals and in accordance with the guidelines of the USF Institutional Animal Care and Use Committee.

Behavioral Tests—Spatial learning and memory performance was tested for each mouse using the Radial Arm Water Maze (RAWM) test. The RAWM was carried out in a 100-cm circular pool with six swim alleys radiating from a common circular swim area. A submerged escape platform was placed near the end of a different arm for each day of testing, which forces mice to use working memory to perform this task. For each trial, the mice were placed in the designated start arm facing the common circular swim area and given 1 minute to find the submerged platform. An error was charged each time a mouse entered an incorrect arm. If the submerged platform was not located during the 1-minute trial, the mouse was guided to the submerged platform and allowed to remain there for 30 seconds before the next trial begins. All mice underwent reference memory training for 7 days with four trials per day. Cognitive ability was assessed as the number of entry-arm errors before finding the platform.

The rotarod task was also performed to exclude the possibility that positive effects of any treatment in RAWM test are due to improvements in Sensorimotor ability. Mice were positioned on the rod (diameter 3.6 cm) of the equipment (Rotarod 7650 accelerating model; Ugo Basile, Biological Research Apparatus, Varese, Italy), which was initially set at 1.0 rpm. The rod was then allowed to steadily accelerate up to 40.0 rpm over a 3-minute session and evaluation was made by monitoring latency to fall.

Immunohistochemistry—Fixed cell cultures and brain sections were stained with indicated antibodies and then treated with donkey anti-mouse IgG conjugated with Alexa Fluor 488 (1:200) and goat anti-rabbit IgG conjugated with Alexa Fluor 594 (1:200; Invitrogen, Carlsbad, Calif., USA). The slides were then washed, mounted with DAPI medium (Vector Laboratories, Burlingame, Calif., USA) and visualized with an Olympus FV1000 confocal microscope (Tokyo, Japan).

Western Blotting (WB) and Analysis—WB analysis was performed as previously described (Modi et al., 2013; Tung et al., 2002). Briefly, the proteins from the various cell-free, cell and brain lysates or homogenates were electrophoretically separated using 10% bicine/tris gel (8 M urea) for proteins less than 5 kD or 10% tricine/tris gels for larger proteins. Electrophoresed proteins were transferred to polyvinylidene difluoride membranes (Bio-Rad, Richmond, Calif., USA), washed and blocked for 2 hours at room temperature in Tris-buffered saline containing 5% (w/v) nonfat dry milk (TBS/NFDM). After blocking, membranes were hybridized for 2 hours with various primary antibodies, washed and incubated for 1 hour with the appropriate HRP-conjugated secondary antibody in TBS/NFDM. Blots were developed using the luminol reagent (Thermo Fisher Scientific, Waltham, Mass., USA).

ELISA—Mouse brains were homogenized in ice-cold lysis buffer for 30 seconds using a Minilys tissue homogenizer (Bertin Technologies, Montigny-le-Bretonneux, France) set at high speed, allowed to stand for 15 minutes at 4° C., and centrifuged at 15,000 rpm for 30 minutes. Soluble $A\beta_{1-40/42}$ species and sAPPα were directly detected in cultured cell media or brain homogenates using the $A\beta_{1-40/42}$ (Invitrogen) and sAPPα ELISA kits (IBL-America, Minneapolis, Minn., USA).

Statistical Analysis—Data are expressed as mean±SD. Comparison between groups was performed by Student's t test or ANOVA followed by LSD or Bonferroni post hoc test. P<0.05 was considered statistically significant.

Example 1

Reduction of Aβ in Chinese Hamster Ovary (CHO) Cells

To examine the effects of various Swedish Tat fusion peptides on Aβ production, human wild-type amyloid precursor protein (APP) is overexpressed in Chinese hamster ovary cells (hereinafter referred to as CHO/APPwt cells), and the cells are treated with either PBS control (Phosphate buffered saline); Swedish peptide-1 (SwePep-1), IKTEEISEVNLDAEFR (also referred herein as "APPsweBBP1") (SEQ ID NO: 5); Swedish peptide-2 (SwePep-2) (also referred herein as "APPsweBBP"), EISEVNLDAEFR (SEQ ID NO: 1); Swedish Tat fusion peptide-1 (SweTatPep-1), YGRKKRRQRRRIKTEEISEVNLDAEFR (also referred herein as "APPsweBBP/TTD1") (SEQ ID NO: 6); or Swedish Tat fusion peptide-2 (SweTatPep-2) (also referred herein as "APPsweBBP/TTD2" and "TAT-APPsweBBP"), YGRKKRRQRRREISEVNLDAEFR (SEQ ID NO: 3). APPsweBBP is a truncated fragment of APPswe spanning 12 amino acid residues (Glu665-Arg676). TAT, an 11-amino acid-residue protein-transduction domain derived from the HIV-1 transactivator of transcription protein, was conjugated at the C-terminus of APPsweBBP and biotin was conjugated at the N-terminus.

Figure 2:
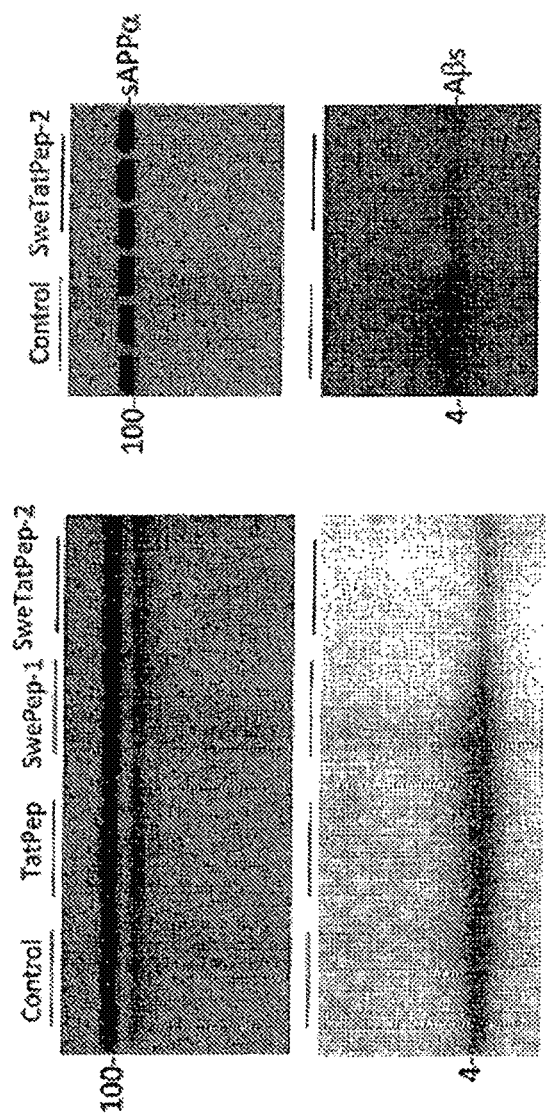
FIG. 2 shows a Western blot of CHO/APPwt cell lysates probed for Aβ expression after treatment with control, TatPep, SwePep-1, and SweTatPep-2 for 12 hours.

Following treatment, Aβ production is determined utilizing ELISA and the results illustrated in FIG. 1A. SweTatPep-2, SwePep-2, SwePep-1 and SweTatPep-1 each reduce Aβ$_{40,42}$ by 63-65%, 30-33%, 31-34% and 37-38%, respectively. SweTatPep-2 (TAT-APPsweBBP) elicited the most effective decrease in Aβ production compared to the other peptides based on ELISA. Furthermore, SweTatPep-2 inhibits Aβ$_{40,42}$ generation in a dose-dependent manner, as shown in FIG. 1B. These results are further shown in Western blot analyses (FIG. 2), where SweTatPep-2 (TAT-APPsweBBP) shows the most effective reduction of Aβ compared with the other peptides tested.

Example 2

Enhanced Reduction of Aβ in Chinese Hamster Ovary (CHO) Cells by Human Swedish Mutant APP BACE1 Binding Peptides Fused to a Tat Protein Transduction Domain To further examine the ability of the Swedish mutant APP BACE1 binding peptide/Tat fusion peptides to decrease Aβ production, CHO cells overexpressing either human wild-type APP (CHO/APPwt cells) or Swedish mutant APP (hereinafter referred to as "CHO/APPswe cells") are treated with a variety of APP-based BACE1 inhibitor peptides, as shown in Table 1 and Table 2. Aβ production is determined using ELISA. The APPsweBBP/TTD2 peptide elicits the most effective decrease in Aβ production compared to the other peptides, reducing Aβ$_{40}$ by 60-70%, Aβ$_{42}$ by 50-60% and increasing sAPPα by 30-40% in both CHO/APPswe cells (Table 1) and CHO/APPwt cells (Table 2).

TABLE 1

CHO cells over-expressing human Swedish mutant APP (CHO/APPswe) were treated with APPsweBBP/TTD2 peptides or a range of control peptides as indicated at 20 μg/mL for 24 hours followed by determination of Aβ and sAPPα production in the cultured media by ELISA. Data presented as mean ± SD. These results are representative of three independent experiments with triplicates for each condition.

| | Secreted Aβ$_{40}$ (ng/mg; mean ± SD) | Secreted Aβ$_{42}$ (ng/mg; mean ± SD) | Secreted sAPPα (ng/mg; mean ± SD) |
|---|---|---|---|
| APPwtBBP1 (IKTEEISEVKMDAEFR) (SEQ ID NO: 7) | 62.43 ± 9.43 | 8.91 ± 0.83 | 217.35 ± 17.32 |
| APPwtBBP (EISEVKMDAEFR) (SEQ ID NO: 4) | 59.84 ± 11.23 | 9.78 ± 1.07 | 201.65 ± 11.54 |
| APPwtBBP3 (EVKMDAEFR) (SEQ ID NO: 8) | 61.36 ± 8.34 | 10.93 ± 1.98 | 199.83 ± 14.65 |
| APPsweBBP1 (IKTEEISEVNLDAEFR) (SEQ ID NO: 5) | 57.23 ± 11.65 | 9.01 ± 1.07 | 211.43 ± 18.31 |
| APPsweBBP2 (EISEVNLDAEFR) (SEQ ID NO: 1) | 41.41 ± 8.43 | 6.54 ± 0.85 | 253.56 ± 20.11 |
| APPsweBBP3 (EVNLDAEFR) (SEQ ID NO: 9) | 57.32.43 ± 7.33 | 7.12 ± 0.84 | 231.26 ± 14.28 |
| APPwtBBP/TTD1 (YGRKKRRQRRRIKTEEISEVKMDAEFR) (SEQ ID NO: 10) | 64.21 ± 12.12 | 7.82 ± 0.67 | 229.45 ± 12.73 |

TABLE 1-continued

CHO cells over-expressing human Swedish mutant APP (CHO/APPswe) were treated with APPsweBBP/TTD2 peptides or a range of control peptides as indicated at 20 μg/mL for 24 hours followed by determination of Aβ and sAPPα production in the cultured media by ELISA. Data presented as mean ± SD. These results are representative of three independent experiments with triplicates for each condition.

|  | Secreted Aβ$_{40}$ (ng/mg; mean ± SD) | Secreted Aβ$_{42}$ (ng/mg; mean ± SD) | Secreted sAPPα (ng/mg; mean ± SD) |
|---|---|---|---|
| APPwtBBP/TTD2 (*YGRKKRRQRRR*EISEVKMDAEFR) (SEQ ID NO: 11) | 40.32 ± 8.43 | 6.78 ± 0.92 | 267.92 ± 15.88 |
| APPwtBBP/TTD3 (*YGRKKRRQRRR*EVKMDAEFR) (SEQ ID NO: 12) | 57.45 ± 13.11 | 9.56 ± 1.11 | 201.23 ± 21.23 |
| APPsweBBP/TTD1 (*YGRKKRRQRRR*IKTEEISEVNLDAEFR) (SEQ ID NO: 6) | 44.89.43 ± 6.87 | 7.98 ± 0.81 | 236.32 ± 13.09 |
| APPsweBBP/TTD2 (*YGRKKRRQRRR*EISEVNLDAEFR) (SEQ ID NO: 3) | 22.12 ± 4.87 | 4.15 ± 0.57 | 359.35 ± 21.23 |
| APPsweBBP/TTD3 (*YGRKKRRQRRR*EVNLDAEFR) (SEQ ID NO: 13) | 41.87 ± 5.76 | 8.43 ± 0.95 | 211.37 ± 18.93 |
| TAT (*YGRKKRRQRRR*) (SEQ ID NO: 2) | 66.71 ± 12.02 | 10.76 ± 2.12 | 196.98 ± 17.77 |

TABLE 2

CHO cells over-expressing human wild-type APP (CHO/APPwt) were treated with APPsweBBP/TTD2 or a range of control peptides at 20 μg/mL for 24 hours followed by examination of Aβ and sAPPα production in the cultured media by ELISA. Data presented as mean ± SD. These results are representative of three independent experiments with triplicates for each condition.

|  | Secreted Aβ$_{40}$ (ng/mg; mean ± SD) | Secreted Aβ$_{42}$ (ng/mg; mean ± SD) | Secreted sAPPα (ng/mg; mean ± SD) |
|---|---|---|---|
| APPwtBBP1 (IKTEEISEVKMDAEFR) (SEQ ID NO: 7) | 11.23 ± 0.89 | 1.23 ± 0.043 | 4874.42 ± 174.56 |
| APPwtBBP2 (EISEVKMDAEFR) (SEQ ID NO: 4) | 10.89 ± 0.76 | 1.18 ± 0.051 | 4762.21 ± 164.89 |
| APPwtBBP3 (EVKMDAEFR) (SEQ ID NO: 8) | 11.43 ± 1.01 | 1.09 ± 0.061 | 4699.78 ± 178.43 |
| APPsweBBP1 (IKTEEISEVNLDAEFR) (SEQ ID NO: 5) | 9.67 ± 0.84 | 1.07 ± 0.054 | 4711.83 ± 201.45 |
| APPsweBBP2 (EISEVNLDAEFR) (SEQ ID NO: 1) | 7.01 ± 1.02 | 0.73 ± 0.034 | 5201.64 ± 119.63 |
| APPsweBBP3 (EVNLDAEFR) (SEQ ID NO: 9) | 10.23 ± 0.73 | 0.92 ± 0.041 | 4709.43 ± 123.74 |
| APPwtBBP/TTD1 (*YGRKKRRQRRR*IKTEEISEVKMDAEFR) (SEQ ID NO: 10) | 9.32 ± 0.68 | 1.01 ± 0.052 | 4688.12 ± 109.65 |

TABLE 2-continued

CHO cells over-expressing human wild-type APP (CHO/APPwt) were treated with APPsweBBP/TTD2 or a range of control peptides at 20 μg/mL for 24 hours followed by examination of Aβ and sAPPα production in the cultured media by ELISA. Data presented as mean ± SD. These results are representative of three independent experiments with triplicates for each condition.

|  | Secreted $A\beta_{40}$ (ng/mg; mean ± SD) | Secreted $A\beta_{42}$ (ng/mg; mean ± SD) | Secreted sAPPα (ng/mg; mean ± SD) |
|---|---|---|---|
| APPwtBBP/TTD2 (TAT-APPwtBBP) (*YGRKKRRQRRR*EISEVKMDAEFR) (SEQ ID NO: 11) | 6.53 ± 0.81 | 0.68 ± 0.034 | 5291.14 ± 142.75 |
| APPwtBBP/TTD3 (*YGRKKRRQRRR*EVKMDAEFR) (SEQ ID NO: 12) | 10.12 ± 1.11 | 10.32 ± 0.042 | 4699.15 ± 155.92 |
| APPsweBBP/TTD1 (*YGRKKRRQRRR*IKTEEISEVNLDAEFR) (SEQ ID NO: 6) | 8.93 ± 0.82 | 0.95 ± 0.037 | 4901.54 ± 211.54 |
| APPsweBBP/TTD2 (*YGRKKRRQRRR*EISEVNLDAEFR) (SEQ ID NO: 3) | 2.43 ± 0.18 | 0.41 ± 0.012 | 6865.73 ± 312.45 |
| APPsweBBP/TTD3 (*YGRKKRRQRRR*EVNLDAEFR) (SEQ ID NO: 13) | 8.74 ± 0.55 | 0.93 ± 0.048 | 5001.45 ± 271.34 |
| TAT (*YGRKKRRQRRR*) (SEQ ID NO: 2) | 11.32 ± 0.45 | 1.07 ± 0.057 | 4766.34 ± 198.34 |

Example 3

TAT-APPsweBBP Binds to and Competitively Inhibits BACE1 Activity

As a required enzyme for the generation of neurotoxic Aβ from APP, BACE1 is well established as an important mediator of AD β-amyloid pathology. As such, it has become an important target for new disease modifying therapeutics. However, since BACE1 also has important physiological roles, abolishment of the enzyme or its activity may lead to deleterious side effects as evidenced by numerous failed clinical trials discussed previously. Thus, it was endeavored to instead find an alternative substrate for BACE1 that does not lead to pathological amyloidosis. Since previous studies have established a close relationship between α-helix structure and peptide-protein (or protein-protein) interactions (Azzarito, 2013; Rao et al., 2013), several APP based peptides were synthesized that might serve as a preferable substrate for BACE1. Importantly, these peptides were free of the Aβ-containing segment and, thus, cannot be amyloidogenic. In theory, these could be used to "hijack" the BACE1 processing of endogenous APP and lead to a decrease in cerebral Aβ. These BACE1 substrates and controls were incubated with recombinant BACE1 and percent of inhibition of the enzyme was calculated. As shown in Table 3, compared to the wild-type APP fragment APPwtBBP, the BACE1 inhibiting activity of APPsweBBP was much greater, although the percentage inhibition was still low (~40%). These data show that APPswe fragments containing Swedish mutant sites exert much higher affinity to BACE1 than their wild-type homologues. Moreover, once the cell penetrating TAT domain was fused with APPsweBBP, yielding TAT-APPsweBBP, its BACE1 inhibitory activity was dramatically elevated (from 38.43 to over-90% inhibition, FIG. 3), and was much higher than the elevation observed with APPwtBBP (elevated by TAT fusion from 16.23 to 21.01%, Table 3). These findings indicate that the α-helical TAT fusion domain may help to promote selective APPsweBBP proteolysis by BACE1, yielding substrate competition against human wild-type APP.

TABLE 3

BACE1 inhibitory activity of APP-based BACE1 binding site peptides. A screen for β-site amyloid precursor protein cleaving enzyme 1 (BACE1) inhibitory activity of various APP-based BACE1 binding peptides demonstrated that TAT-APPsweBBP is most active as evidenced by 93.23% ± 2.73% inhibition.

| APP based BACE1 binding site peptides (APPBBP) | % of inhibition (mean ± SD) |
|---|---|
| APPwt$^a$BBP (EISEVKMDAEFR) SEQ ID NO: 4 | 16.23 ± 0.29 |
| APPwt$^a$BBP3 (EVKMDAEFR) SEQ ID NO: 8 | 4.89 ± 0.06 |
| APPswe$^b$BBP (EISEVNLDAEFR) SEQ ID NO: 1 | 38.43 ± 1.01 |
| APPswe$^b$BBP3 (EVNLDAEFR) SEQ ID NO: 9 | 14.32 ± 0.04 |
| TAT-APPwt$^a$BBP (*YGRKKRRQRRR*EISEVKMDAEFR) SEQ ID NO: 11 | 21.01 ± 1.42 |

TABLE 3-continued

BACE1 inhibitory activity of APP-based BACE1 binding site peptides. A screen for β-site amyloid precursor protein cleaving enzyme 1 (BACE1) inhibitory activity of various APP-based BACE1 binding peptides demonstrated that TAT-APPsweBBP is most active as evidenced by 93.23% ± 2.73% inhibition.

| APP based BACE1 binding site peptides (APPBBP) | % of inhibition (mean ± SD) |
|---|---|
| TAT-APPswe[b]BBP (<u>YGRKKRRQRRR</u>EISEVNLDAEFR) SEQ ID NO: 3 | 93.23 ± 2.73 |
| TAT (<u>YGRKKRRQRRR</u>) SEQ ID NO: 2 | 3.32 ± 0.02 |

[a]wild-type APP;
[b]swedish mutant APP

Figure 4:
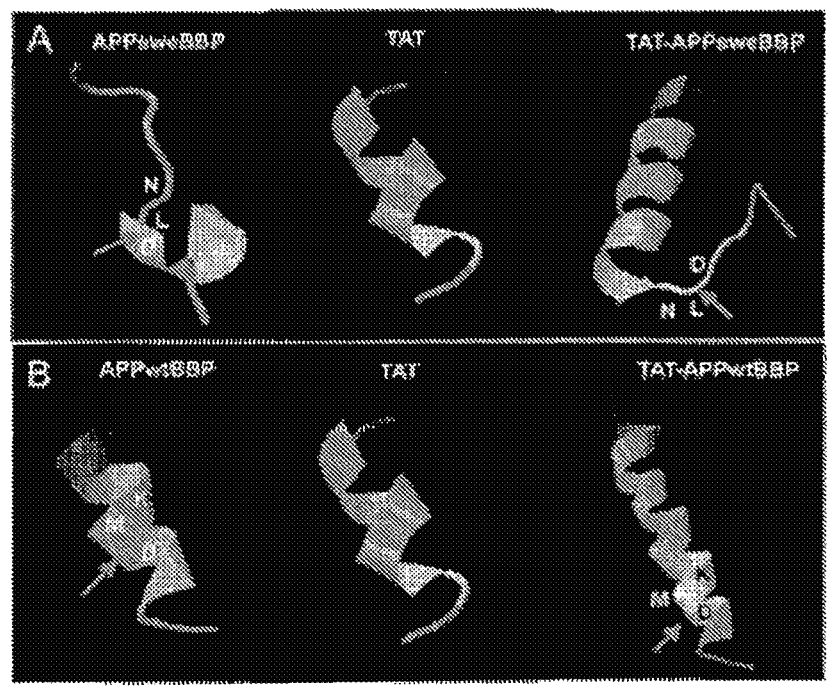
FIG. 4 shows three-dimensional (3-D) structure analysis to further predict the potential interactions between TAT-APPsweBBP and BACE1, 3-D structure modeling and enzyme-substrate interactions were analyzed via online server Mobyle@RPBS v1.5.1 (http://mobylespbs.univ-paris-diderot.fr/). The modeling suggested that after fusion with HIV-1 TAT protein transduction domain, the resulting TAT-APPsweBBP possesses more α-helices than APPsweBBP alone (A). Moreover, the less folded BACE1 cleavage site of TAT-APPsweBBP outside the α-helix (L-D, arrow), may create a less sterically hindered and larger site for BACE1 binding, higher binding affinity and more efficient enzymatic digestion compared to TAT-APPwtBBP (B, M-D, arrow). Owing to more α-helical content, the β-cleavage site of TAT-APPwtBBP is less accessible within the α-helix structure. This 3-D structure analysis predicts that TAT-APPsweBBP strongly and effectively interacts with BACE1.
Figure 15:
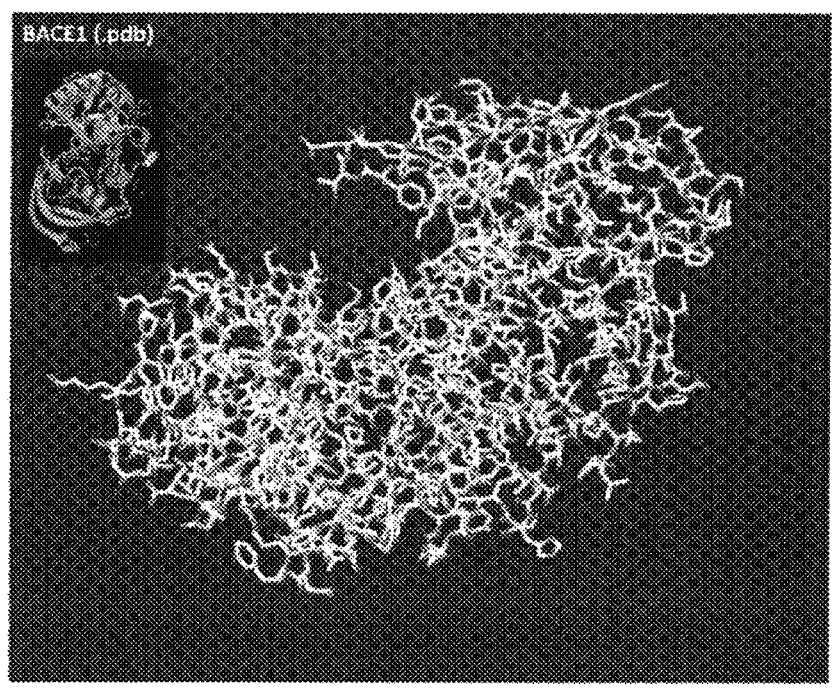
FIG. 15 shows a 3-D structure model of BACE1.
Figure 16:
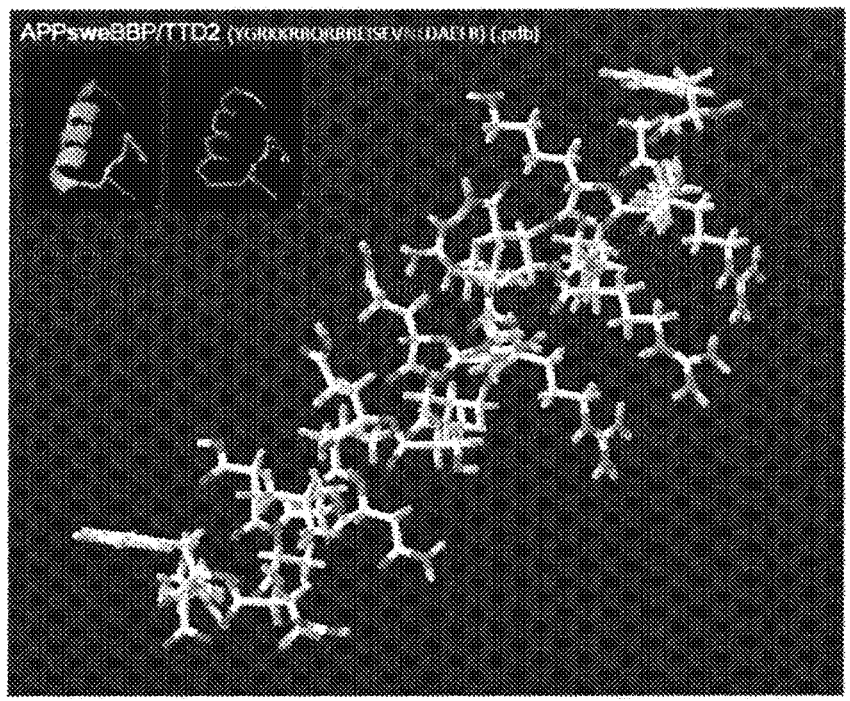
FIG. 16 shows a 3-D structure model of APPsweBBP/TTD2 (TAT-APPsweBBP).
Figure 17:
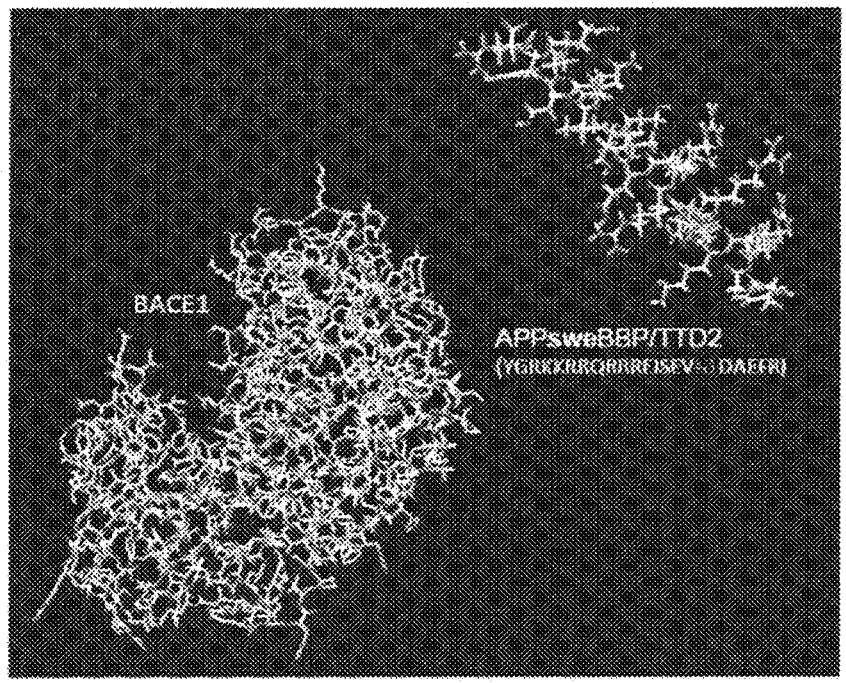
FIG. 17 shows a 3-D structure model of both BACE1 and BACE1 inhibiting peptide APPsweBBP/TTD2.
Figure 18:
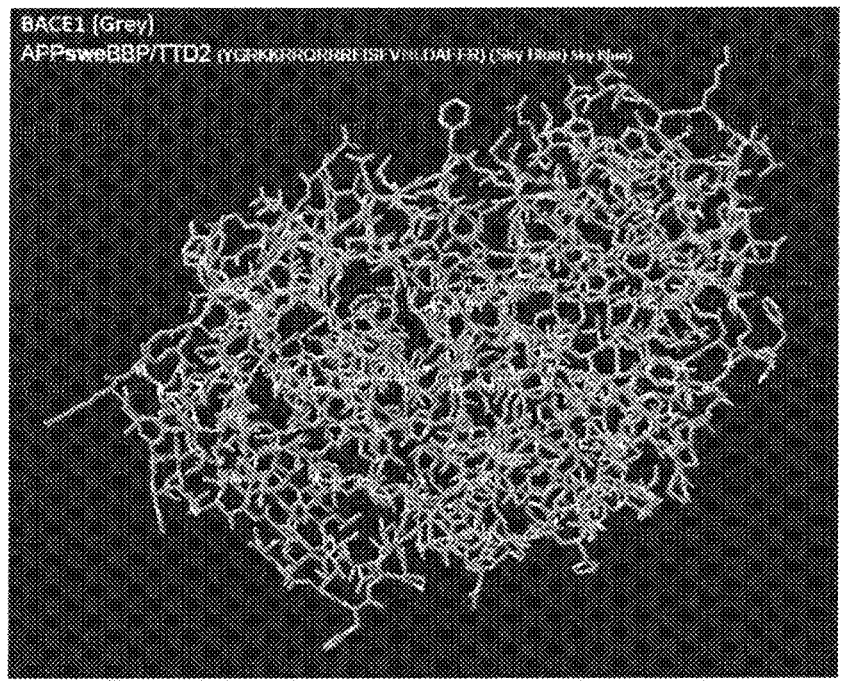
FIG. 18 shows a 3-D structure model of BACE1-APPsweBBP/TTD2 protein interaction.
Figure 19:
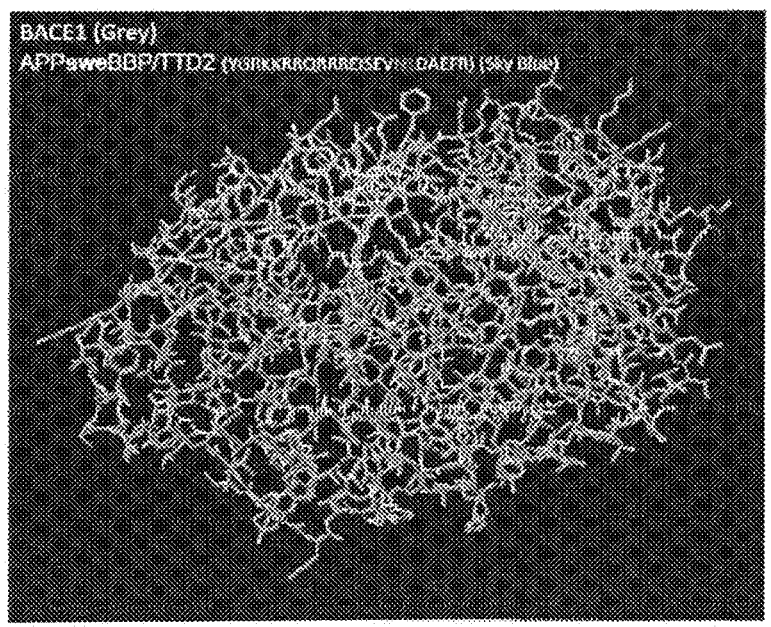
FIG. 19 shows a 3-D structure model of BACE1-APPsweBBP/TTD2 protein interaction.
Figure 20:
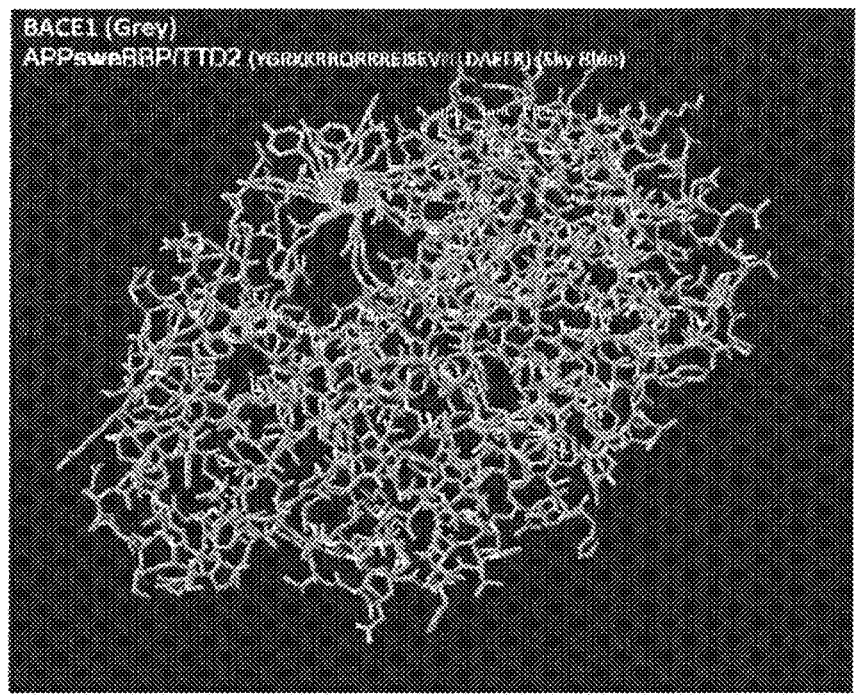
FIG. 20 shows a 3-D structure model of BACE1-APPsweBBP/TTD2 protein interaction.
Figure 21:
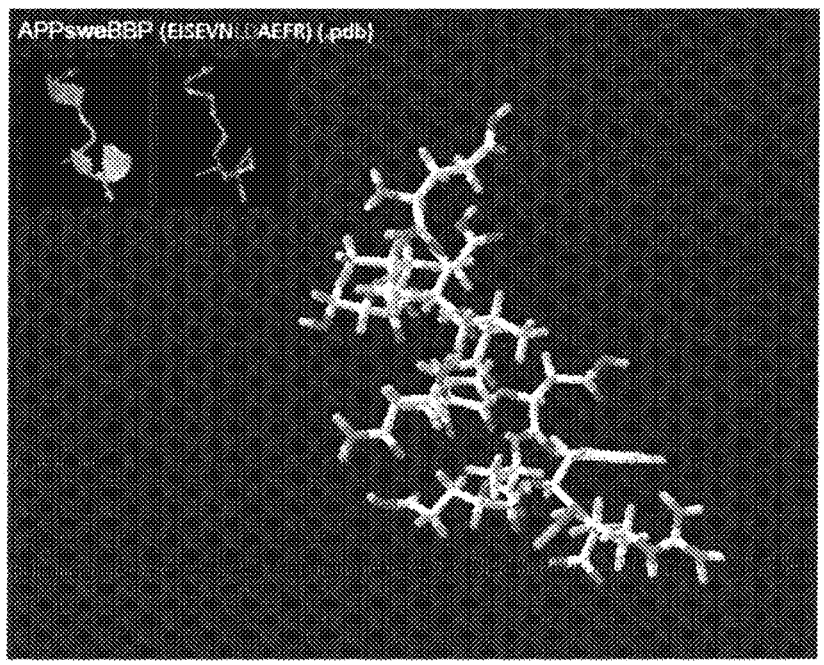
FIG. 21 shows a 3-D structure model of APPsweBBP.
Figure 22:
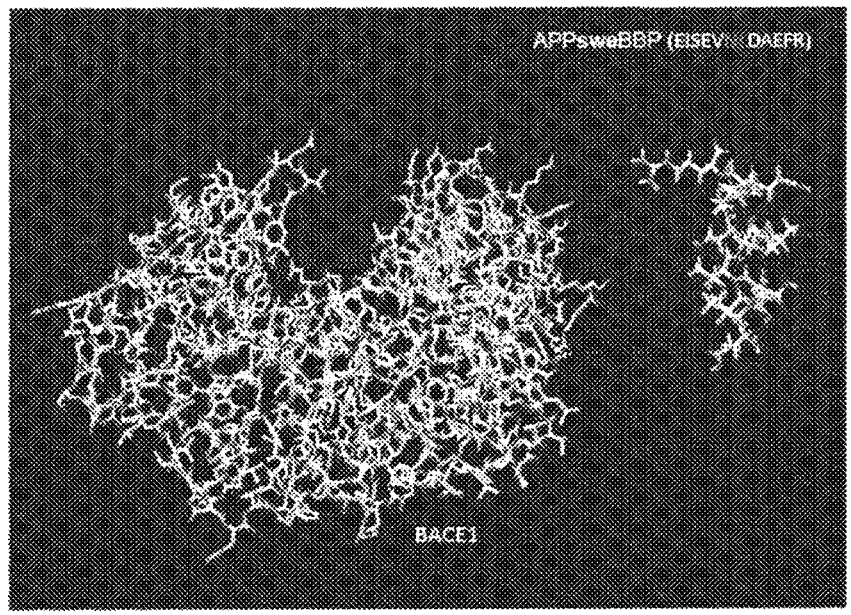
FIG. 22 shows 3-D structure models of both BACE1 and APPsweBBP.
Figure 23:
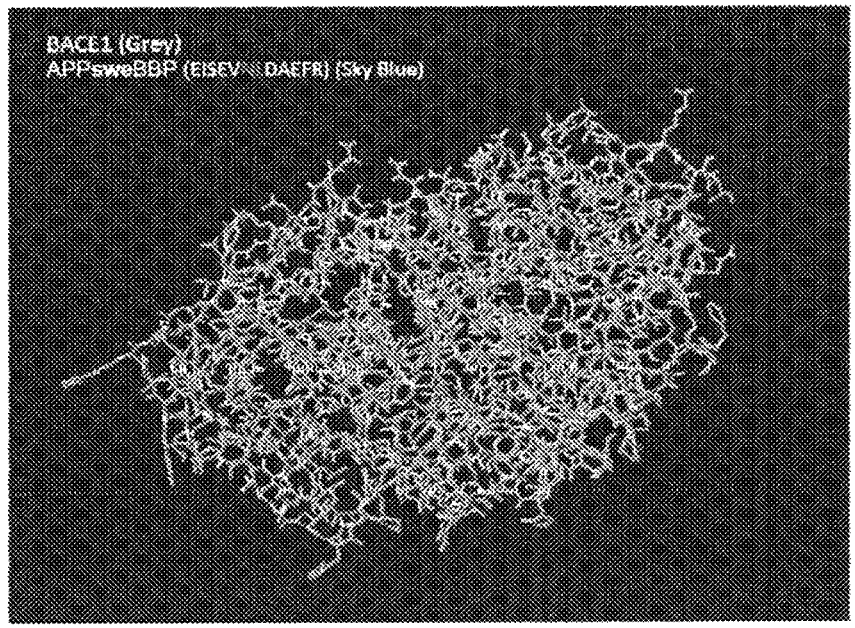
FIG. 23 shows 3-D structure model of BACE1-APPsweBBP protein interaction.
Figure 24:
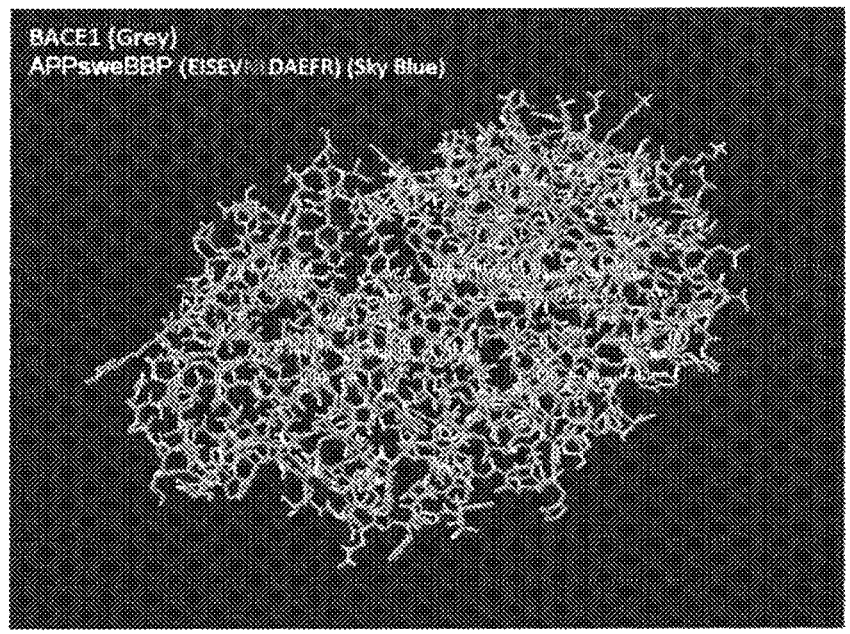
FIG. 24 shows 3-D structure model of BACE1-APPsweBBP protein interaction.
Figure 25:
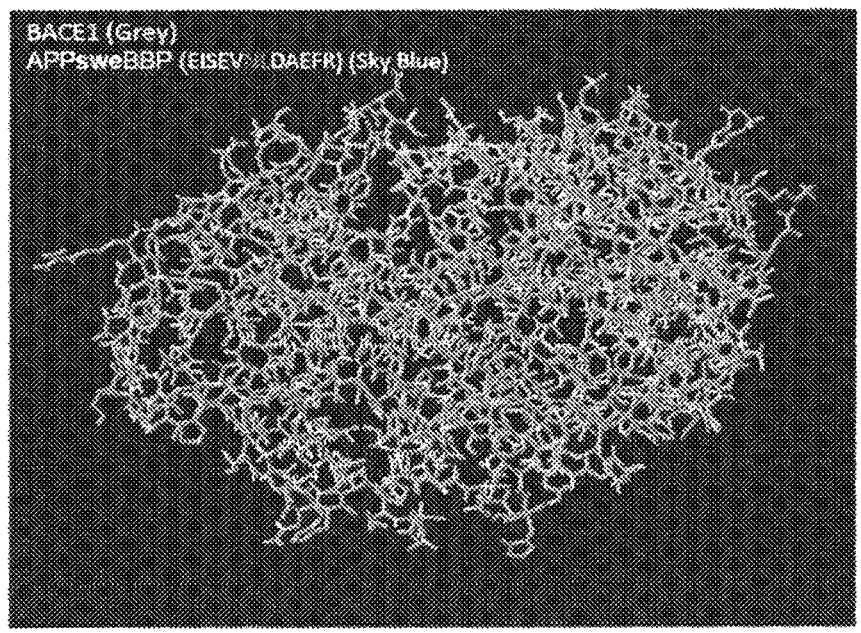
FIG. 25 shows 3-D structure model of BACE1-APPsweBBP protein interaction.

These results were further confirmed using 3-D structure modeling via the online server Mobyle@RPBS v1.5.1. The results of this analysis (FIG. 4) suggested that after fusion with the HIV-1 TAT protein transduction domain, TAT-APPsweBBP assumes more alpha helical structure than APPsweBBP itself, suggesting more potential interaction with BACE1. Furthermore, TAT-APPsweBBP left the BACE1 cleavage site (L-D) exposed outside the α helix (FIG. 4, panel A), allowing less sterical hinderance for BACE1 binding and more efficient enzymatic digestion compared to APPsweBBP. In contrast, owing to more α-helical structure, the β-cleavage site (M-D) of TAT-APPwtBBP is less accessible compared with TAT-APPsweBBP (FIG. 4, panel B). The in vitro and in vivo efficacy of the newly identified superior BACE1 substrate, TAT-APPsweBBP, was further evaluated, which could potentially prevent cerebral amyloidosis with minimal adverse events. See also FIGS. 15-25 for in silico 3-D structure analysis (Protein Data Bank files generated by Avogadro V1.1.0) of BACE1 (FIG. 15, 17), TAT-APPsweBBP (FIG. 16, 17), TAT-APPsweBBP-BACE1 protein-interaction (FIGS. 18, 19, and 20), APPsweBBP (FIG. 21), APPsweBBP and BACE1 (FIG. 22), and BACE1 interaction with APPsweBBP (FIGS. 23-25). This in silico analysis further confirms that the TAT-APPsweBBP-BACE1 protein-interaction has a different binding mode versus APPsweBBP. It appears the α-helix structure of the TAT-fused peptide TAT-APPsweBBP favors binding to BACE1 in a manner that folds the β-cutting-sites into the helix, which results in the β-cut site becoming much less accessible as it is bound up in this helix. As a result, there is reduced β-cleavage of endogenous APP and, thus, a "hijack" (i.e., sequestering) of BACE1 by TAT-APPsweBBP in terms of its ability to produce Aβ specifically, as the in vitro studies herein also indicate. Meanwhile, APP protein is free to undergo normal alpha cleavage since BACE1 is effectively inhibited by TAT-APPsweBBP.

Figure 5:
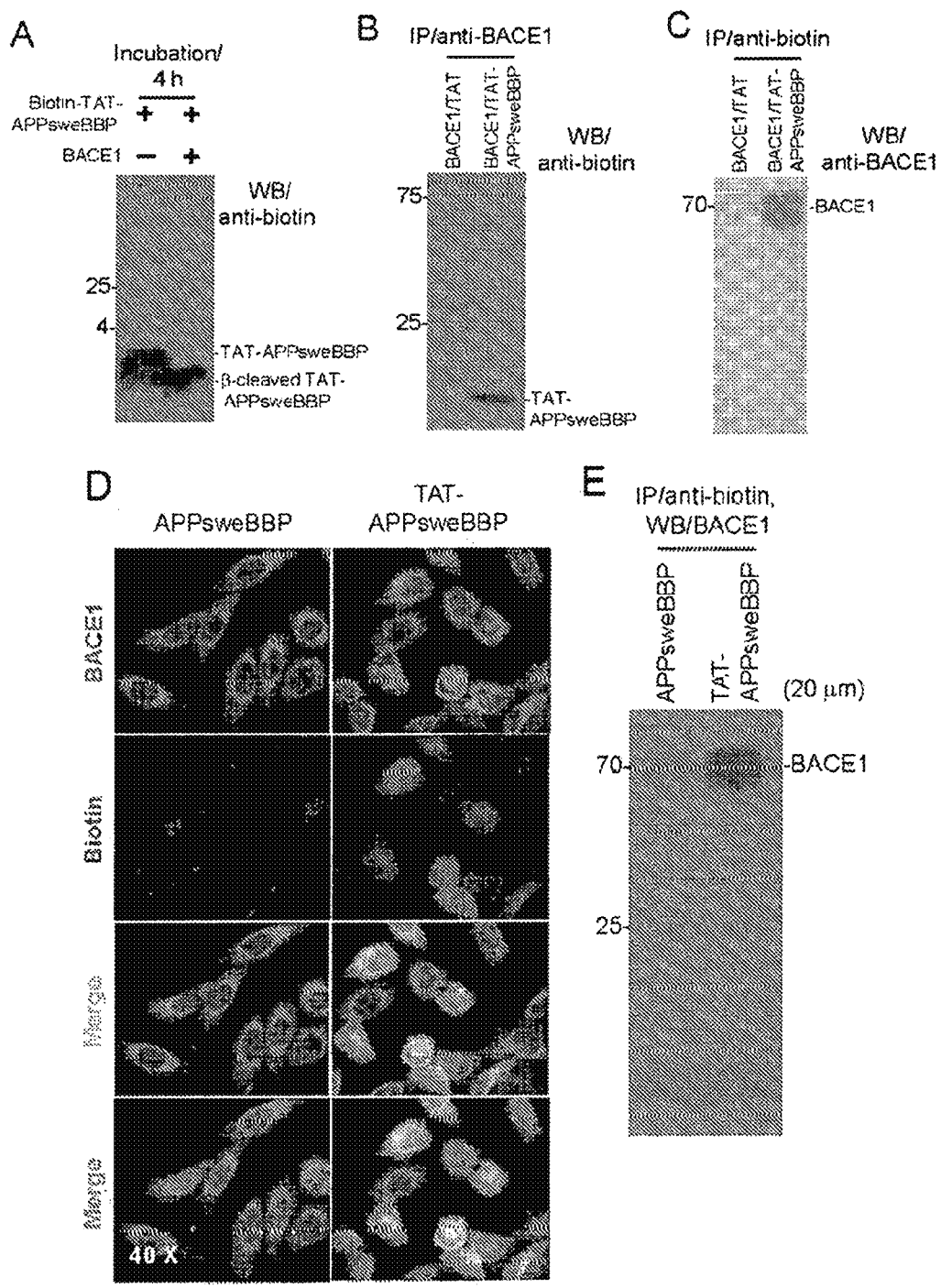
FIG. 5 shows Western blot (WB) and immunohistochemical analyses indicating that TAT-APPsweBBP strongly binds to and is cleaved by BACE1. Biotin-labeled TAT-APPsweBBP was incubated with or without recombinant BACE1 protein and examined by western blot (A). Full length TAT-APPsweBBP and β-cleaved TAT-APPsweBBP were clearly detected. Immunoprecipitation (IP) with anti-BACE1 antibody and subsequent WB with anti-biotin antibody (B) and IP with anti-biotin antibody and then WB with anti-BACE1 antibody (C) both reveal that TAT-APPsweBBP, but not TAT peptide, binds to BACE1. To further confirm TAT-APPswcBPP can bind to BACE1, human wild-type APP expressing CHO cells were incubated with biotin-labeled TAT-APPsweBBP or biotin-labeled APPsweBBP at 20 μM for 30 minutes, and then stained with anti-BACE1 or anti-biotin antibodies (D). TAT-APPsweBPP showed a strong association with BACE1 in both cytoplasmic membrane and intracellular compartments. In addition, these treated cells were further analyzed by IP with anti-biotin and subsequent WB with anti-BACE1 antibodies (E), with results showing that TAT-APPsweBBP strongly and specifically binds to BACE1.

In order to further confirm the interactions of TAT-APPsweBBP with BACE1, biotin-labeled TAT-APPsweBBP (TAT-APPsweBBP-biotin) was co-incubated with recombinant BACE1 protein for 4 hours. Subsequent Western blot (WB) analysis clearly revealed BACE1 mediated conversion of full length TAT-APPsweBBP-biotin to the slightly lower molecular weight β-cleaved TAT-APPsweBBP-biotin fragment (FIG. 5A). Furthermore, immunoprecipitation (IP) analysis of the mixture with anti-BACE1 IP followed by anti-biotin WB (FIG. 5B) or anti-biotin IP followed by anti-BACE1 WB (FIG. 5C) revealed that TAT-APPsweBBP binds to BACE1 protein, while such binding was not observed with biotin-labeled TAT peptide alone. Therefore, TAT-APPsweBBP associates with and is cleaved by BACE1.

Example 4

TAT-APPsweBBP Inhibits Aβ Generation In Vitro

Next, the ability of TAT-APPsweBBP to interact with BACE1 in cell cultures was tested. CHO/APPwt cells were incubated with biotin-labeled TAT-APPsweBBP or APPsweBBP at 20 μM for 30 minutes, followed by staining with anti-BACE1 and anti-biotin antibodies. It was found that TAT-APPsweBBP was much more strongly co-localized with BACE1 protein compared with APPsweBBP in both cytoplasmic membrane and intracellular compartments (FIG. 5D). Subsequent IP analyses of the cell lysate corroborated these findings since TAT-APPsweBBP was markedly bound to BACE1 compared to APPsweBBP (FIG. 5E).

Figure 6:
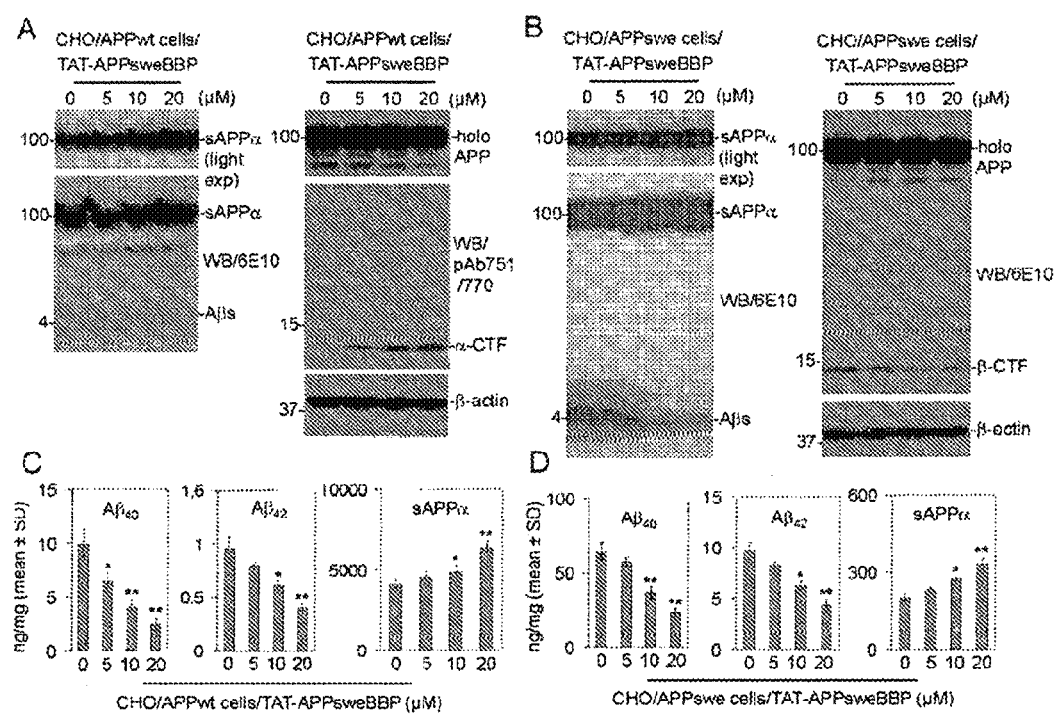
FIG. 6 shows Western blot (WB) and ELISA analyses indicating that TAT-APPsweBBP inhibits APP amyloidogenic processing. CHO cells expressing wild-type human APP (CHO/APPwt) or Swedish mutant human APP (CHO/APPswe) were treated with TAT-APPsweBBP for 24 hours. Cultured media and cell lysates were then prepared for APP processing analysis by WB and ELISA. TAT-APPsweBBP markedly inhibited $A\beta_{1-40/42}$ (A and B, left panels) and β-CTF (B, right panel), while promoting α-CTF (A, right panel) and sAPPα production (A and B, left panels), in a dose-dependent manner in both CHO/APPwt (A) and CHO/APPswe cells (B), while leaving holo APP expression unaltered (A and B, right panels), as determined by WB analysis. Light exposure (light exp) more clearly reveals sAPPα band as examined by 6E10 WB analysis. Consistent with these results, TAT-APPsweBBP significantly decreased $A\beta_{1-40/42}$ and increased sAPPα levels in a dose-dependent manner in both CHO/APPwt (C) and CHO/APPswe cells (D), as determined by ELISA (*P<0.05; **P<0.01). These results are representative of 3 independent experiments with each condition triplicated.

Since a potent BACE1 substrate was identified and it was established that it co-localized with the enzyme in vitro, the therapeutic efficacy of TAT-APPsweBBP for reducing amyloidogenic processing of APP was tested. CHO/APPwt or CHO/APPswe cells were cultured and treated with TAT-APPsweBBP for 24 hours, followed by analysis of APP processing via WB of cellular lysates and media. Indeed, TAT-APPsweBBP potently opposed amyloidogenic processing of APP by BACE1 in a dose-dependent fashion, evidenced by markedly decreased $A\beta_{1-40/42}$ (FIGS. 6A and B, left panels) and β-CTF production (FIG. 6B, right panel), together with increased α-CTF (FIG. 6A, right panel) and sAPPα production (FIGS. 6A and B, left panels). These effects were further supported by Aβ and sAPPα ELISA analyses of CHO/APPwt (FIG. 6C) and CHO/APPswe cells (FIG. 6D). As expected, however, the CHO/APPswe cells produced comparatively greater levels of $A\beta_{1-40/42}$ and lesser levels of sAPPα than the CHO/APPwt cells since the Swedish mutation possesses greater affinity for BACE1.

Example 5

TAT-APPsweBBP Penetrates the BBB and Reduces AD Behavioral and Pathological Changes Considering a potent BACE1 substrate was identified and its anti-amyloidogenic efficacy was established in vitro, its efficacy in vivo was evaluated next. For these experiments, a 5XFAD transgenic mouse model of AD was utilized, which has five familial AD mutations, 3 human APP and 2 human PS1 mutations, as first described by Oakley et al. (Oakley et al., 2006). These mice exhibit typical hallmark AD pathology by 2 months of age, including Aβ aggregates, neurodegeneration and neuronal loss, and significant behavioral deficits by 4-5 months of age, at an accelerated rate, which makes them ideal for rapidly assessing the efficacy of potential AD therapeutics.

The hypothesis that TAT-APPsweBBP would more effectively penetrate the BBB compared with APPsweBBP alone was initially tested. 5XFAD mice at 2 months of age (n=5, female) were treated with biotin-labeled TAT-APPsweBBP or APPsweBBP (100 nM/kg, i.p.) daily for 5 days and then euthanized 4 hours after the last injection. Brain tissues were removed, sectioned, and stained with anti-BACE1 and anti-biotin antibodies. Confocal images revealed that the peripherally administered TAT-APPsweBBP indeed highly penetrated the BBB and was detectable in both the cortical and hippocampal regions of the 5XFAD mice (FIG. 7), in contrast with peripherally administered APPsweBBP. This highlights the importance of the membrane fusion fragment of the HIV-1 Tat protein (TAT) for cerebral delivery of APPsweBBP.

Then, the efficacy of TAT-APPsweBBP for opposing behavioral and amyloidogenic pathologies typical of 5XFAD mice was tested. To this end, 5XFAD and wild-type (WT) mice were randomized into three treatment groups as follows: (1) TAT-APPsweBBP-treated, (2) TAT-peptide-treated and (3) PBS-injected (control) mice. Each mouse was treated with TAT-APPsweBBP, TAT or PBS i.p. daily for eight consecutive weeks and then subjected to the radial arm water maze (RAWM) and rotarod tests (FIG. 8A). In the RAWM test, TAT-APPsweBBP-treated 5XFAD mice committed significantly fewer errors during training between days 3-5 and 7-10, respectively, compared with TAT- and PBS-treated mice (FIG. 8B, top panel), indicating that TAT-APPsweBBP alleviated cognitive impairment. In contrast, WT mice exhibited no difference among the various treatment groups (FIG. 8B, bottom panel). Although all mice demonstrated increased latency to fall after 2 days of rotarod testing, there were no differences between treatment groups on each day for either 5XFAD or WT mice (FIGS. 8C and D). Therefore, TAT-APPsweBBP treatment did not improve motor performance.

Figure 9:
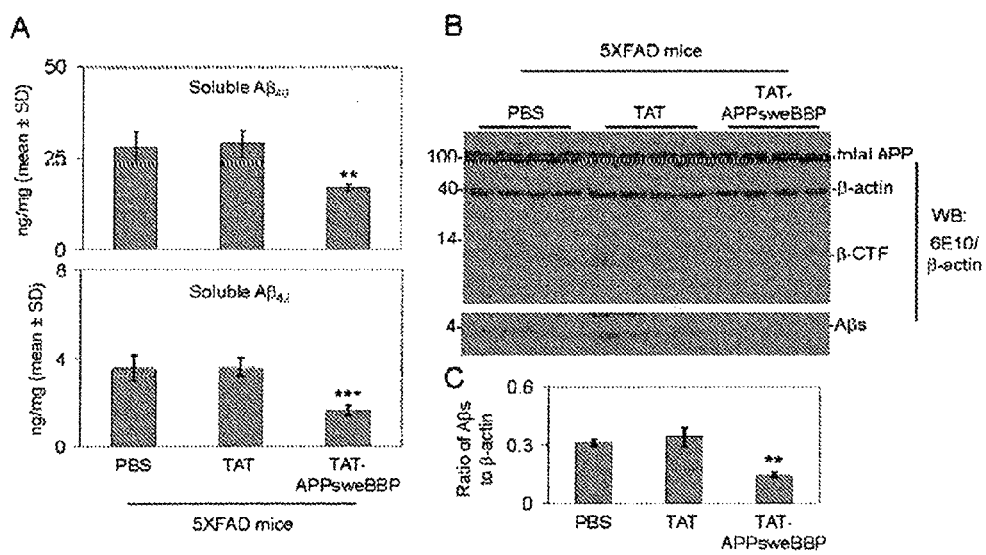
FIG. 9 shows ELISA and Western blot (WB) analyses indicating that TAT-APPsweBBP markedly inhibits APP amyloidogenic processing in 5XFAD mice. 5XFAD mice were euthanized after 8 weeks of treatment, followed by preparation of brain homogenates for biochemical analyses. TAT-APPsweBBP treatment significantly reduced detergent-soluble $A\beta_{1-40/42}$ levels by 41% and 54%, respectively, compared to TAT peptide- or PBS-treatments, as assessed by ELISA (A, $P<0.01$; *$P<0.005$). Data are represented as mean±SD of $A\beta_{1-40/42}$ (ng/mg of total protein). In addition, TAT-APPsweBBP reduced total cerebral soluble Aβ (Aβs) and β-CTF, as determined by WB with 6E10, without significantly altering total APP expression (B). The WB was re-probed with anti-β-actin antibody. Densitometry analysis reveals that TAT-APPsweBBP significantly reduces the band density ratios of total cerebral Aβ to β-actin compared to TAT peptide- and PBS-treatments (C). Data are represented as mean±SD.
Figure 10:
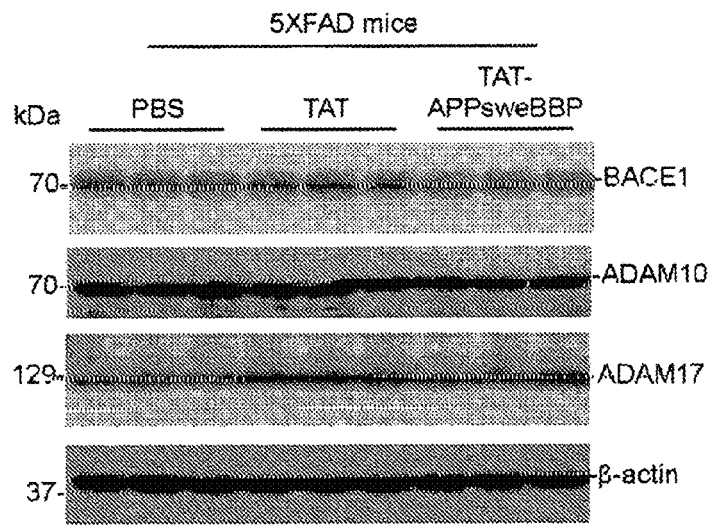
FIG. 10 shows Western blot (WB) of BACE1, ADAM10 and ADAM17 expression levels in brain homogenates of TAT-APPsweBBP-, TAT- and PBS-treated 5XFAD mice. The expression levels of BACE1, ADAM10 and ADAM17 were not significantly different between TAT-APPsweBBP-, TAT- or PBS-treated mice, as determined by WB analysis.

In addition to cognitive testing, neuronal APP proteolysis was also evaluated by ELISA and WB. Given the findings in vitro that TAT-APPsweBBP exerted BACE1 inhibitory and anti-amyloidogenic effects, it was hypothesized that one would see similar results in 5XFAD mice. The ELISA analysis revealed statistically significant decreases in soluble $A\beta_{1-40/42}$ levels in TAT-APPsweBBP-treated compared to TAT peptide- or PBS-treated 5XFAD mice (FIG. 9A). Moreover, WB analysis indicated that TAT-APPsweBBP-treated 5XFAD mice showed much lower levels of APP amyloidogenic processing products, such as β-CTF and Aβs, compared to TAT peptide- and PBS-treated mice without notable alteration on total APP expression (FIGS. 9B and C). In addition, the BACE1, ADAM10, and ADAM17 expressions in brain homogenates of these mice was examined using WB, and no significant changes in the expression levels of these three proteins between TAT-APPswcBBP-, TAT- or PBS-treated mice was observed (FIG. 10).

Figure 11:
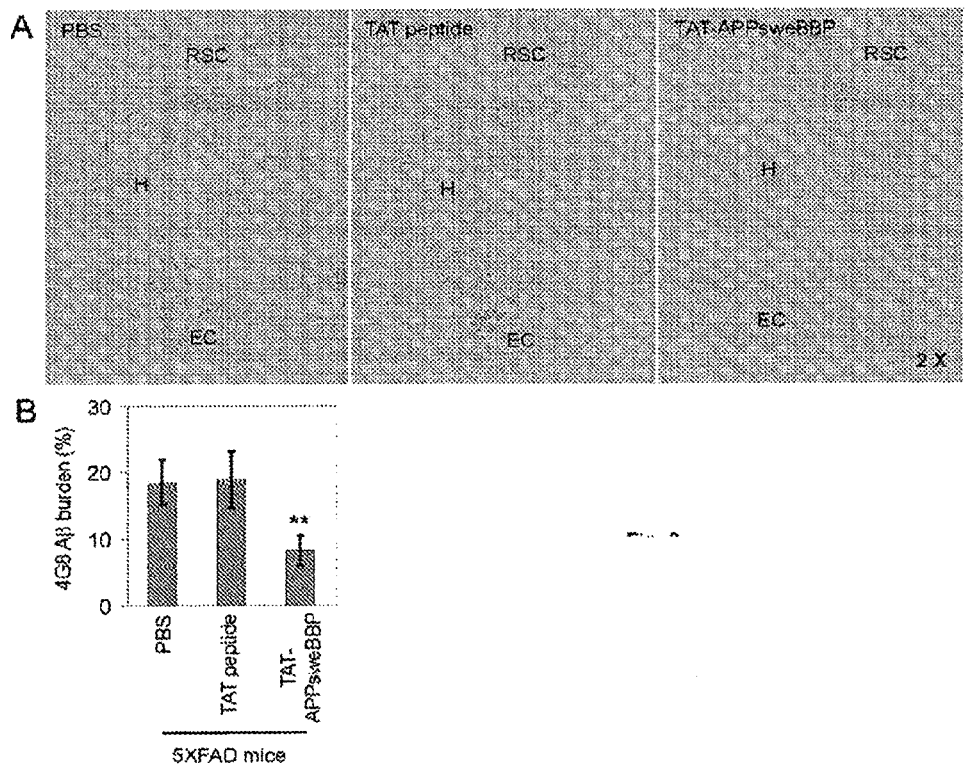
FIG. 11 shows immunohistochemical staining and image analysis indicating that TAT-APPsweBBP markedly reduces β-amyloid deposits. TAT-APPsweBBP markedly reduced β-amyloid plaques in retrosplenial cortex (RSC), entorhinal cortex (EC) and hippocampus (H) regions of 5XFAD mouse brains, as determined by immunohistochemical staining with anti-$A\beta_{16-26}$ antibody (4G8, A). Percentage of 4G8 immunoreactive areas in regions of interest (RSC, EC and H regions) was quantified by image analysis for each treatment group (B). Data are represented as mean±SD (n=10, 5 female/5 male). A t test for independent samples revealed significant differences between TAT-APPsweBBP and TAT peptide treatment groups (**$P<0.01$), but no significant difference between TAT peptide and PBS groups ($P>0.05$).

Since cerebral β-amyloid deposits have been a common finding in AD and other neurodegenerative diseases, the effects of peripheral TAT-APPsweBBP treatment on this AD marker was also studied in the 5XFAD mice. Immunohistochemical staining with anti-$A\beta_{16-26}$ antibody (4G8) indicated a marked reduction of β-amyloid plaques in retrosplenial cortex (RSC), entorhinal cortex (EC) and hippocampus (H) regions of 5XFAD mouse brains (FIG. 11A). Moreover, image analysis revealed that the percentage of 4G8 Aβ antibody immunoreactive areas in regions of interest (RSC, EC, and H regions) were greatly reduced in the TAT-APPsweBBP treated mice compared to the TAT and PBS treatment groups (FIG. 11B).

DISCUSSION

BACE1 is found in a number of tissues throughout the body but the majority of its expression is in the brain (Lin et al., 2000). The importance of BACE1 and its influence on AD has been investigated thoroughly since it was first identified in 1999 (Vassar et al., 1999; Hussain et al., 1999). The proteolytic cleavage of APP by BACE1 produces a soluble Aβ fragment, which has the ability to aggregate and migrate onto the dendrites and cell bodies of neuronal cells, initiating chronic immune responses of inflammation and microglial activation. Without early identification and effective inhibition of this pathogenic pathway, the disease is anticipated to become more widespread with the current rapid increase in prevalence within the elderly. Previous study has suggested an endogenous negative-feedback mechanism whereby the proteolytic product of non-amyloidogenic processing of APP, sAPPα, inhibited BACE1-mediated amyloidogenic APP cleavage in a mouse model (Obregon et al., 2012). This resulted in an overall reduction in Aβ formation under physiological conditions. Importantly, the consequence of the BACE1 proteolytic pathway being impaired in any way could result in a decrease in APP amyloidogenic processing.

Attempts to inhibit BACE1 have been relatively fruitless with most therapeutic trials being aborted in the early stages (Yan et al., 2014). A number of obstacles must be overcome in the development of such inhibitors, such as those relating to solubility, bioavailability, potency, and effectiveness. In addition, there are also a number of substrates cleaved by BACE1 which are important in other pathways which regulate voltage gated sodium channels and axon myelination (Wong et al., 2005; Hu et al., 2006). For example, BACE1 KO mice exhibit hypomyelination, mediated by reduced neuregulin-Akt signaling and myclinating protein levels (Hu et al., 2006). This can create adverse reactions beyond the reduction of plaques (Yan et al., 2014; Willem et al., 2006). The new-generation BACE1 inhibitory candidates with novel therapeutic strategies were therefore required.

Figure 12:
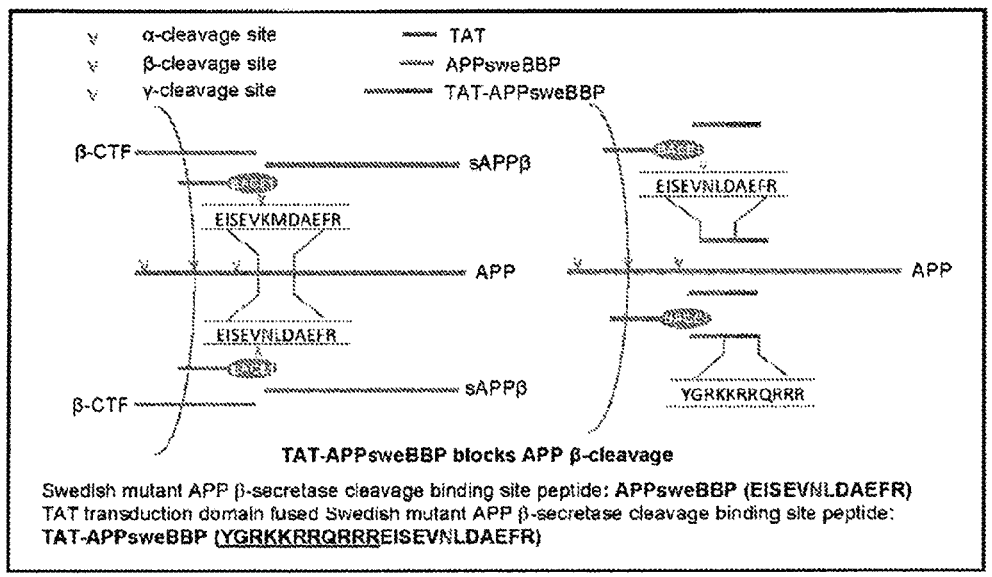
FIG. 12 shows an illustration of the competitive inhibition of BACE1 endogenous APP cleavage by TAT-APPsweBBP. BACE1 cleaves APP at the β-cleavage site, with higher efficacy for APPswe (EISEVNLDAEFR) (SEQ ID NO: 1) than APPwt (EISEVKMDAEFR) (SEQ ID NO: 4), yielding β-CTF and sAPPβ. β-CTF is then further cleaved at the γ-site to yield Aβ. TAT-APPsweBBP, a BACE1 binding site peptide derived from APPswe (EISEVNLDAEFR) (SEQ ID NO: 1) and fused with TAT transduction domain (YGRKKRRQRRR) (SEQ ID NO: 2), competitively blocks BACE1 cleavage of APPwt abrogating Aβ production.

The present invention shows that manipulation of BACE1 with natural peptides as opposed to synthetic chemical inhibitors may be a novel and safer strategy for BACE1 targeted therapeutics (FIG. 12). Furthermore, with the roles of BACE1 in proteolysis of many natural substrates, complete chemical inhibition of BACE1 could result in undesirable off-target effects. This is especially true in light of the fact that APP may not even be the primary substrate of the enzyme (Probst et al., 2012). Therefore, specific inhibition of only the APP β-cleavage, but not complete inhibition of BACE1 function, may be the most appropriate therapy to normalize the increased APP-directed BACE1 activity seen in AD patients.

Figure 8:
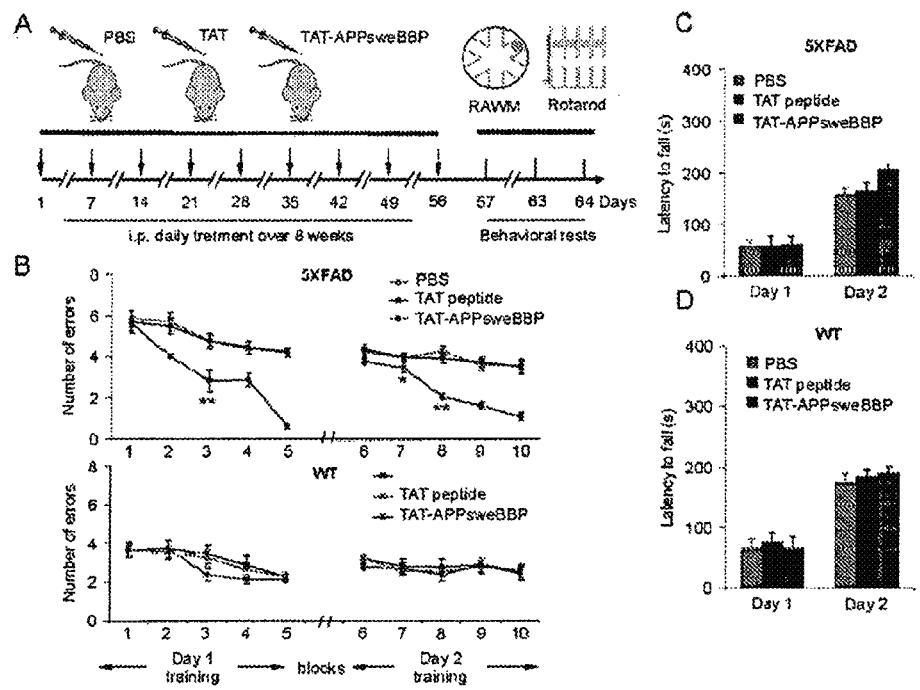
FIG. 8 shows behavioral learning and memory analyses in mice indicating that peripherally administered TAT-APPsweBBP improves hippocampal-dependent learning and memory in 5XFAD mice. In order to correlate the BACE1 inhibitory activities of TAT-APPsweBBP with improved cognitive function, 5XFAD and WT control mice were randomized into three treatment groups: (1) TAT-APPsweBBP treated, (2) TAT peptide-treated and (3) phosphate-buffered saline (PBS)-injected mice (n=10 per treatment, 5 female/5 male). The mice were treated with TAT-APPsweBBP, TAT-peptide (100 nM/kg in 100 μL PBS) or PBS i.p. daily for 8 weeks. Following the treatment, hippocampal-dependent behavioral learning and memory was assessed with the radial arm water maze (RAWM, schedule as illustrated in A). Cognitive ability was assessed as the number of entry-arm errors before finding the platform. Compared to PBS or TAT-treatments, TAT-APPsweBBP enhanced cognitive ability, as evidenced by fewer errors (B). In contrast there was no significant difference between WT treatment groups. Sensorimotor ability was also assessed using rotarod test in 5XFAD (C) and WT control (D) mice after treatment. TAT-APPsweBBP treatment tended to enhance motor activity in 5XFAD mice, as shown by increased latency to fall, but this did not reach a statistical level of significance when compared to either TAT peptide- or PBS-treated mice. All data are presented as mean±SD (*$P<0.05$; **$P<0.01$, repeated measures analysis of variance (ANOVA) with LSD (B) or Bonferroni post hoc test (C and D).
Figure 13:
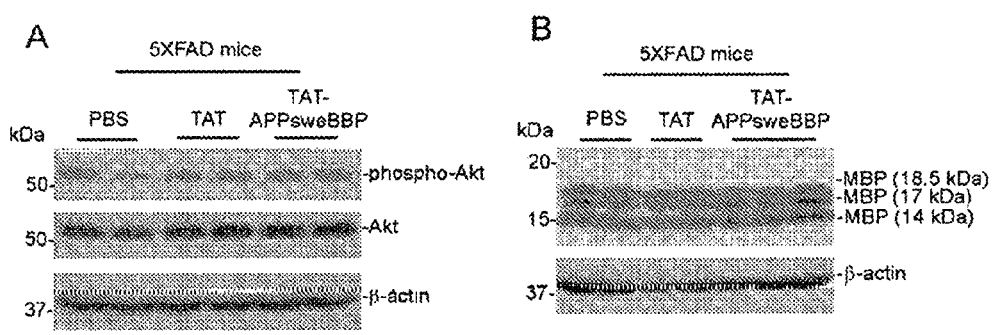
FIG. 13 shows Western blot (WB) for Aid phosphorylation state and MBP expression levels with specific antibodies against total and phosphorylated Akt (A) and MBP protein (B). Total Akt, phosphorylated Akt and MBP expression levels in brain homogenates did not differ between TAT-APPsweBBP-, TAT- and PBS-treated 5XFAD mice.

In the present invention, data from a cell-free BACE1 activity assay clearly indicated APPsweBBP competitively inhibits the binding of commercial BACE1 substrate (EVN-LDAEFK) to BACE1 (Table 3). Moreover, TAT-APPsweBBP showed much higher inhibiting activity than its prototype peptide (FIG. 3), indicating a positive role of the TAT conjugation in BACE1 inhibition. Data from IP and WB analyses also indicated that, after binding with BACE1 (FIGS. 5B and C), TAT-APPsweBBP can also be cleaved (FIG. 5A), indicating that TAT-APPsweBBP elicits a functional inhibition of BACE1 in contrast to recently developed non-cleavable substrate-based peptidomimetics. APPsweBBP reduced BACE1-mediated APP amyloidogenesis both in vitro (FIG. 6) and in 5XFAD mice (FIG. 9), while also reducing cognitive impairment (FIG. 8). In addition, APPsweBBP did not alter myelin signaling, observed as unchanged Aid phosphorylation and myelin basic protein levels (FIG. 13), confirming that APPsweBBP specifically reduces BACE1 activity without eliciting side effects.

It should be noted that a previous study developed a series of BACE1 inhibitors designed from substrate-based peptide sequences to competitively inhibit its binding regions and shut off its enzymatic properties (Tung et al., 2002). The initial peptide sequences showed promise with high potency and selectivity but did not progress as a viable pharmaceutical target because they were large and unstable. Indeed, one of these peptides, OM99-2 (EVNLA*AEF), was reported to be too large (>18 amino acids residues) to cross the BBB and also not stable enough for use in therapeutic trials (Hong et al., 2000), even though the peptide did have a high level of potency. These studies show that substrate-based anti-BACE1 peptide-therapeutics may fulfill the desired properties required for an inhibitor, with the issue being BBB transport.

Figure 3:
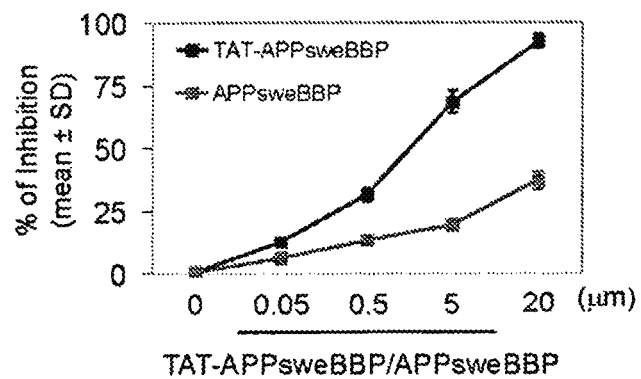
FIG. 3 shows a graph of BACE1 percentage inhibition assayed in the absence and presence of APPsweBBP or TAT-APPsweBBP at 0.05, 0.5, 5 and 20 μM.
Figure 7:
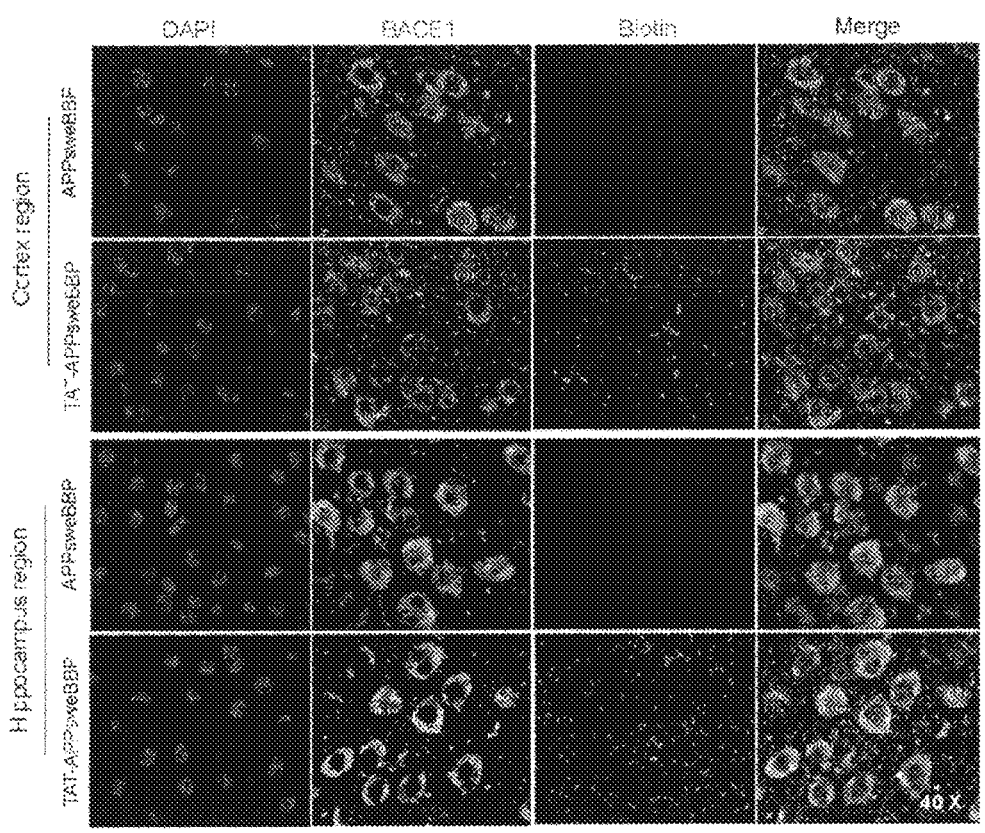
FIG. 7 shows immunohistochemical analyses indicating that TAT-APPsweBBP highly penetrates the blood brain barrier (BBB) after intraperitoneal (i.p) administration in 5XFAD mice. In order to determine the BBB permeability of TAT-APPsweBBP, biotin-labeled TAT-APPsweBBP or APPsweBBP (100 nM/kg in 100 μl physiological saline) was intraperitoneally (i.p.) administered daily to 5XFAD mice at 2 months of age for 5 days (n=5, female). The mice were euthanized 4 hours after the last injection and then brain tissues were removed, sectioned and stained with anti-BACE1 and anti-biotin antibodies. Alexa Fluor® 594 donkey anti-rabbit IgG was used to detect the biotin signal and Alexa Fluor® 488 goat anti-mouse IgG was used to detect the BACE1 signal. All images were taken with an Olympus Fluoview FV1000 laser scanning confocal microscope. Results show that TAT-APPsweBBP is more permeable across the BBB and more highly associates with BACE1 compared to APPsweBBP. No noticeable differences in biotin distribution were observed between 5XFAD and WT control mice following either biotin-labeled TAT-APPsweBBP or APPsweBBP injection (data not shown).
Figure 14:
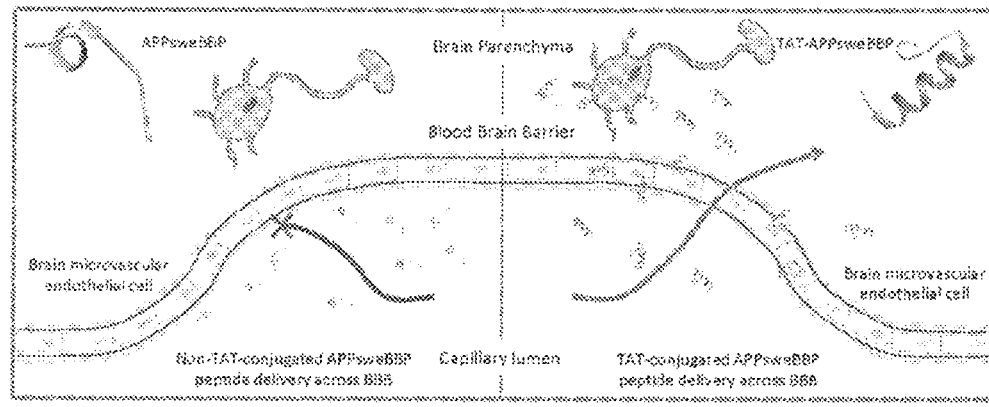
FIG. 14 shows an illustration of TAT (47-57) peptide conjugation facilitation of APPsweBBP penetration across BBB. Peripherally injected TAT-APPsweBBP freely enters brain microvascular endothelial cells and crosses the BBB from the capillary lumen into the brain parenchyma, while APPsweBBP is stopped at the capillary lumen.

Indeed, good BBB penetration creates a challenge that goes beyond the production of protein specific intervention strategics. In particular, the drug needs to maintain an ability to inhibit BACE1, maintain solubility and cross the tight junctions of the brain's vascular endothelium. To overcome this challenge, the HIV-1 TAT fusion domain, which has been demonstrated to favor intracellular delivery and efficient penetration through the BBB (Cooper et al., 2012), was conjugated to the novel competitive substrate-based BACE1 inhibitor of the present invention. It was hypothesized that conjugation of this α-helical peptide to the BACE1 inhibitor of the present invention would not only favor its crossing the BBB but also favor it's binding with BACE1 (FIG. 14). As shown in previous studies, a close relationship exists between the α-helical structure and peptide-protein (or protein-protein interactions (Azzarito et al., 2013; Rao et al., 2013). The 3-dimension structure prediction in the present invention (generated by Mobyle@RPBS v1.5.1) suggested that TAT-conjugation indeed enhances the α-helical structure of APPsweBBP (FIG. 4), while the cell-free assay indicated that this conjugation enhanced the inhibitory potency of this peptide (FIG. 3). The in vivo study of the present invention further supports the hypothesis, as evidenced by greater distribution of TAT-APPsweBBP-biotin than APPsweBBP into cortical and hippocampal regions after 5-days systemic administration (FIG. 7).

Taken together, the data shows that one can use the higher affinity of APPswe for the design of a peptide, APPsweBBP, for competitive and specific inhibition of the BACE1 APP cleavage site. By coupling this peptide to TAT, it is found to exhibit enhanced efficacy for BACE1 inhibition as well as enhanced BBB penetration, decreasing the production of Aβ both in vitro and in vivo. Underlying this may be a conformational change promoted by fusion of APPsweBBP with the TAT fusion domain, thereby favoring interaction of APPsweBBP with BACE1. Since TAT-APPsweBBP lacks the intact Aβ domain, it "hijacks" endogenous wild-type APP binding to BACE1 due to its greater affinity (Haass et al., 1995; Thinakaran et al., 1996), thereby reducing the cleavage of endogenous wild-type APP without concurrent Aβ generation. Although future studies should confirm that no other substrates of BACE1 are affected by TAT-APPsweBBP, the present invention provides a novel strategy for design of BACE1 inhibitors and provides that TAT-APPsweBBP may be a novel, safe, and effective APP substrate-based BACE1 inhibitor. Given that accumulation of toxic species of Aβ as well as their deposition into cerebral plaques may play an important role in the development of AD and other neurodegenerative diseases, use of the TAT-APPsweBBP peptide (YGRKKRRQRRREISEVN-LDAEFR) (SEQ ID NO: 3) and similar peptides is useful for the treatment or prevention of AD and other amyloid-related disorders.

All publications and patent documents cited in this application are incorporated by reference in pertinent part for all purposes to the same extent as if each individual publication or patent document were so individually denoted. By citation of various references in this document, Applicant does not admit any particular reference is "prior art" to their invention. It is to be appreciated that the Detailed Description section, and not the Abstract section, is intended to be used to interpret the claims. The Abstract section may set forth one or more but not all exemplary embodiments of the present invention as contemplated by the inventor(s), and thus, are not intended to limit the present invention and the appended claims in any way.

The foregoing description of the specific embodiments should fully reveal the general nature of the invention so that others can, by applying knowledge within the skill of the art, readily modify and/or adapt for various applications such specific embodiments, without undue experimentation, without departing from the general concept of the present invention. Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents. Moreover, the breadth and scope of the present invention should not be limited by any of the above-described exemplary embodiments, but should similarly be defined only in accordance with the following claims and their equivalents.

REFERENCES

1. D. J. Selkoe, Translating cell biology into therapeutic advances in Alzheimer's disease. *Nature* 399, A23 (Jun. 24, 1999).
2. S. Sinha, I. Lieberburg, Cellular mechanisms of beta-amyloid production and secretion. *Proceedings of the National Academy of Sciences of the United States of America* 96, 11049 (Sep. 28, 1999).
3. D. Games et al., Alzheimer-type neuropathology in transgenic mice overexpressing V717F beta-amyloid precursor protein. *Nature* 373, 523 (Feb. 9, 1995).
4. L. S. Higgins, B. Cordell, Transgenic mice and modeling Alzheimer's disease. *Reviews in the neurosciences* 6, 87 (April-June, 1995).
5. D. Seiffert et al., Presenilin-1 and -2 are molecular targets for gamma-secretase inhibitors. *The Journal of biological chemistry* 275, 34086 (Nov. 3, 2000).
6. M. S. Wolfe et al., Two transmembrane aspartates in presenilin-1 required for presenilin endoproteolysis and gamma-secretase activity. *Nature* 398, 513 (Apr. 8, 1999).
7. J. Shen et al., Skeletal and CNS defects in Presenilin-1-deficient mice. *Cell* 89, 629 (May 16, 1997).
8. P. C. Wong et al., Presenilin 1 is required for Notch1 DII1 expression in the paraxial mesoderm. *Nature* 387, 288 (May 15, 1997).
9. C. Haass, B. De Strooper, The presenilins in Alzheimer's disease—proteolysis holds the key. *Science* 286, 916 (Oct. 29, 1999).
10. W. P. Esler et al., Transition-state analogue inhibitors of gamma-secretase bind directly to presenilin-1. *Nature cell biology* 2, 428 (July, 2000).
11. C. Haass, Take five—BACE and the gamma-secretase quartet conduct Alzheimer's amyloid beta-peptide generation. *The EMBO journal* 23, 483 (Feb. 11, 2004).
12. V. Cone et al., Safety and tolerability of the gamma-secretase inhibitor avagacestat in a phase 2 study of mild to moderate Alzheimer disease. *Archives of neurology* 69, 1430 (November, 2012).

13. R. C. Green et al., Effect of tarenflurbil on cognitive decline and activities of daily living in patients with mild Alzheimer disease: a randomized controlled trial. *JAMA: the journal of the American Medical Association* 302, 2557 (Dec. 16, 2009).
14. R. S. Doody et al., A phase 3 trial of semagacestat for treatment of Alzheimer's disease. *The New England journal of medicine* 369, 341 (Jul. 25, 2013).
15. N. F. Schor, What the halted phase III gamma-secretase inhibitor trial may (or may not) be telling us. *Annals of neurology* 69, 237 (February, 2011).
16. V. B. Gupta, V. K. Gupta, R. Martins, Semagacestat for treatment of Alzheimer's disease. *The New England journal of medicine* 369, 1660 (Oct. 24, 2013).
17. M. Ohno et al., BACE1 deficiency rescues memory deficits and cholinergic dysfunction in a mouse model of Alzheimer's disease. *Neuron* 41, 27 (Jan. 8, 2004).
18. H. Cai et al., BACE1 is the major beta-secretase for generation of Abeta peptides by neurons. *Nature neuroscience* 4, 233 (March, 2001).
19. L. Hong et al., Structure of the protease domain of memapsin 2 (beta-secretase) complexed with inhibitor. *Science* 290, 150 (Oct. 6, 2000).
20. Z. N. Zhu et al., Discovery of Cyclic Acylguanidines as Highly Potent and Selective beta-Site Amyloid Cleaving Enzyme (BACE) Inhibitors: Part I-Inhibitor Design and Validation. *J Med Chem* 53, 951 (Feb. 11, 2010).
21. D. F. Wyss et al., Combining NMR and X-ray Crystallography in Fragment-Based Drug Discovery: Discovery of Highly Potent and Selective BACE-1 Inhibitors. *Top Curr Chem* 317, 83 (2012).
22. A. K. Ghosh, H. L. Osswald, BACE1 (beta-secretase) inhibitors for the treatment of Alzheimer's disease. *Chemical Society reviews*, (Apr. 2, 2014).
23. D. Oehlrich, H. Prokopcova, H. J. Gijsen, The evolution of amidine-based brain penetrant BACE1 inhibitors. *Bioorganic & medicinal chemistry letters* 24, 2033 (May 1, 2014).
24. G. Evin, G. Lessene, S. Wilkins, BACE inhibitors as potential drugs for the treatment of Alzheimer's disease: focus on bioactivity. *Recent Patents CNS Drug Discov* 6, 91 (2011).
25. G. Probst, Y. Z. Xu, Small-molecule BACE1 inhibitors: a patent literature review (2006-2011). *Expert opinion on therapeutic patents* 22, 511 (May, 2012).
26. R. Yan, R. Vassar, Targeting the beta secretase BACE1 for Alzheimer's disease therapy. *Lancet neurology* 13, 319 (March, 2014).
27. Y. Luo et al., Mice deficient in BACE1, the Alzheimer's beta-secretase, have normal phenotype and abolished beta-amyloid generation. *Nature neuroscience* 4, 231 (March, 2001).
28. K. Nishitomi et al., BACE1 inhibition reduces endogenous Abeta and alters APP processing in wild-type mice. *Journal of neurochemistry* 99, 1555 (December, 2006).
29. M. Willem et al., Control of peripheral nerve myelination by the beta-secretase BACE1. *Science* 314, 664 (Oct. 27, 2006).
30. E. Giacobini, G. Gold, Alzheimer disease therapy-moving from amyloid-beta to tau. *Nat Rev Neurol* 9, 677 (December, 2013).
31. K. Rezai-Zadeh et al., Green tea epigallocatechin-3-gallate (EGCG) modulates amyloid precursor protein cleavage and reduces cerebral amyloidosis in Alzheimer transgenic mice. *J Neurosci* 25, 8807 (Sep. 21, 2005).
32. V. Modi, D. Lama, R. Sankararamalcrishnan, Relationship between helix stability and binding affinities: molecular dynamics simulations of Bfl-1/A1-binding pro-apoptotic BH3 peptide helices in explicit solvent. *J Biomol Struct Dyn* 31, 65 (Jan. 1, 2013).
33. S. R. Schwarze, A. Ho, A. Vocero-Akbani, S. F. Dowdy, In vivo protein transduction: delivery of a biologically active protein into the mouse. *Science* 285, 1569 (Sep. 3, 1999).
34. G. D. Cao et al., In vivo delivery of a Bcl-xL fusion protein containing the TAT protein transduction domain protects against ischemic brain injury and neuronal apoptosis. *Neurosci* 22, 5423 (Jul. 1, 2002).
35. L. L. Zou, J. L. Ma, T. Wang, T. B. Yang, C. B. Liu, Cell-Penetrating Peptide-Mediated Therapeutic Molecule Delivery into the Central Nervous System. *Curr Neuropharmacol* 11, 197 (March, 2013).
36. V. Azzarito, K. Long, N. S. Murphy, A. J. Wilson, Inhibition of alpha-helix-mediated protein-protein interactions using designed molecules. *Nature chemistry* 5, 161 (March, 2013).
37. T. Rao et al., Truncated and Helix-Constrained Peptides with High Affinity and Specificity for the cFos Coiled-Coil of AP-1. *Plos One* 8, (Mar. 27, 2013).
38. H. Oakley et al., Intraneuronal beta-amyloid aggregates, neurodegeneration, and neuron loss in transgenic mice with five familial Alzheimer's disease mutations: potential factors in amyloid plaque formation. *J Neurosci* 26, 10129 (Oct. 4, 2006).
39. X. Lin et al., Human aspartic protease memapsin 2 cleaves the beta-secretase site of beta-amyloid precursor protein. *Proceedings of the National Academy of Sciences of the United States of America* 97, 1456 (Feb. 15, 2000).
40. R. Vassar et al., Beta-secretase cleavage of Alzheimer's amyloid precursor protein by the transmembrane aspartic protease BACE. *Science* 286, 735 (Oct. 22, 1999).
41. I. Hussain et al., Identification of a novel aspartic protease (Asp 2) as beta-secretase. *Mol Cell Neurosci* 14, 419 (December, 1999).
42. D. Obregon et al., Soluble amyloid precursor protein-alpha modulates beta-secretase activity and amyloid-beta generation. *Nature communications* 3, 777 (2012).
43. H. K. Wong et al., beta Subunits of voltage-gated sodium channels are novel substrates of beta-site amyloid precursor protein-cleaving enzyme (BACE1) and gamma-secretase. *The Journal of biological chemistry* 280, 23009 (Jun. 17, 2005).
44. X. Hu et al., Bace1 modulates myelination in the central and peripheral nervous system. *Nature neuroscience* 9, 1520 (December, 2006).
45. J. S. Tung et al., Design of substrate-based inhibitors of human beta-secretase. *J Med Chem* 45, 259 (Jan. 17, 2002).
46. I. Cooper et al., Peptide derived from HIV-1 TAT protein destabilizes a monolayer of endothelial cells in an in vitro model of the blood-brain barrier and allows permeation of high molecular weight proteins. *The Journal of biological chemistry* 287, 44676 (Dec. 28, 2012).
47. C. Haass et al., The Swedish mutation causes early-onset Alzheimer's disease by beta-secretase cleavage within the secretory pathway. *Nature medicine* 1, 1291 (December, 1995).
48. G. Thinakaran, D. B. Teplow, R. Siman, B. Greenberg, S. S. Sisodia, Metabolism of the "Swedish" amyloid precursor protein variant in neuro2a (N2a) cells. Evidence that cleavage at the "beta-secretase" site occurs in the golgi apparatus. *The Journal of biological chemistry* 271, 9390 (Apr. 19, 1996).

The invention claimed is:

1. A peptide consisting of SEQ ID NO: 3, or a variant thereof, wherein the variant consists of no more than 30 amino acids and comprises at least the first 11 amino acids and the last 9 amino acids of SEQ ID NO: 3.

2. A pharmaceutical composition comprising a therapeutically effective amount of the peptide of claim 1 and a pharmaceutically acceptable carrier.

3. A kit comprising the peptide of claim 1 and one or more reagents.

4. A cultured cell comprising the peptide of claim 1.

5. A method of treating, reducing the risk of, lessening the severity of, or delaying the onset of an amyloid-related disorder comprising administering to a subject having the disorder, or who is at risk of the disorder, a therapeutically effective amount of the peptide of claim 1.

6. The method of claim 5, wherein the subject is human.

7. The method of claim 5, wherein the subject is at risk of developing an amyloid-related disorder.

8. The method of claim 5, wherein the amyloid-related disorder is a neurological disease.

9. The method of claim 5, wherein the amyloid-related disorder is selected from the group consisting of Alzheimer's disease, HIV associated neurocognitive impairment, Lewy body dementia, cerebral amyloid angiopathy, inclusion body myositis, and mild cognitive impairment.

10. The method of claim 5, wherein the APP-Tat fusion peptide is in a pharmaceutically acceptable carrier.

* * * * *

UNITED STATES PATENT AND TRADEMARK OFFICE
CERTIFICATE OF CORRECTION

PATENT NO. : 9,926,354 B2  
APPLICATION NO. : 15/107383  
DATED : March 27, 2018  
INVENTOR(S) : Jun Tan et al.

Page 1 of 1

It is certified that error appears in the above-identified patent and that said Letters Patent is hereby corrected as shown below:

On the Title Page

Item (54),
"BASED Ã#-SECRETASE INHIBITOR" should read --BASED β-SECRETASE INHIBITOR--.

In the Specification

Column 1,
Line 2, "BASED Ã#-SECRETASE INHIBITOR" should read --BASED β-SECRETASE INHIBITOR--.

Column 5,
Line 45, "and hippocampus (II) regions" should read --and hippocampus (H) regions--.

Column 8,
Line 10, "APPswe770 iso form)." should read --APPswe770 isoform).--.

Column 14,
Line 60, "anti-Aβ$_{16-26}$ antibody" should read --anti-Aβ16-26 antibody--.

Column 21,
Line 6, "are representativeof three" should read --are representative of three--.

Signed and Sealed this  
Eleventh Day of December, 2018

Andrei Iancu  
*Director of the United States Patent and Trademark Office*